United States Patent [19]

Ducep et al.

[11] Patent Number: 5,097,023

[45] Date of Patent: Mar. 17, 1992

[54] α-GLUCOSIDASE INHIBITORS

[75] Inventors: Jean-Bernard Ducep, Neuf-Brisach; Charles Danzin, Strasbourg, both of France

[73] Assignee: Merrell Dow Pharmaceuticals Inc., Cincinnati, Ohio

[21] Appl. No.: 583,545

[22] Filed: Sep. 17, 1990

[30] Foreign Application Priority Data

Oct. 10, 1989 [EP] European Pat. Off. ........ 89402794.5

[51] Int. Cl.$^5$ ..................... A61K 31/70; C07H 15/26; C07H 19/044
[52] U.S. Cl. ..................... 536/17.4; 514/25; 514/866; 514/909
[58] Field of Search ............... 536/17.4; 514/24, 25, 514/866, 909, 885

[56] References Cited

U.S. PATENT DOCUMENTS 4,639,436  1/1987  Junge et al. .......................... 514/32

OTHER PUBLICATIONS

Grant & Hackh's Chemical Dictionary, Fifth Edition, McGraw-Hill Book Company, N.Y., N.Y. 1987, p. 313.
Fleet et al., *Tetrahedron*, 42, 20, 5685 (1986).
Fleet et al., (FEBS) *Elsevier Science Publishers* B.V., 237 1,2, 128-132 (1988).

*Primary Examiner*—Ronald W. Griffin
*Attorney, Agent, or Firm*—Carolyn D. Moon

[57] ABSTRACT

This invention relates to novel N-glycosyl derivatives of 1,4-dideoxy-1,4-imino-D-arabinitol, to the chemical processes for their preparation, to their α-glucosidase inhibiting properties, and to their end-use application in the treatment of diabetes, obesity and those diseases associated with retroviruses, particularly the HIV virus reported to be the causative of the acquired immune deficiency syndrome (AIDS).

21 Claims, No Drawings

α-GLUCOSIDASE INHIBITORS

This invention relates to novel 1,4-di-deoxy-1,4-imino-D-arabinitol derivatives, to the processes for their preparation and to their end-use applications, particularly as to their use in the treatment of diabetes.

More specifically this invention relates to novel N-glycosyl derivatives of 1,4-dideoxy-1,4-imino-D-arabinitol, to the chemical processes for the preparation, to their α-glucosidase inhibiting properties, and to their end-use application in the treatment of diabetes, obesity and those diseases associated with retroviruses, particularly the HIV virus reported to be the causative of the acquired immune deficiency syndrome (AIDS).

Still more specifically this invention relates to the novel 1,4-dideoxy-1,4-imino-D-arabinitol derivatives of the formula

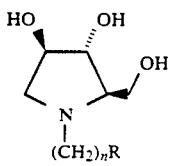

including their optical and geometric isomers, and the pharmaceutically acceptable acid addition salts thereof wherein n is zero, 1, or 2 and R is a glycosyl or etherified or acylated glycosyl radical containing from 1 to 3 hexose or pentose units, said etherified or acylated glycosyl radical bearing the ether or acyl radical at the hydroxyl moiety located on the anomeric carbon atoms.

Acid addition salts are those salts forms with such inorganic acids as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, 2-acetoxybenzoic, mandelic and like acids; and with organic sulfonic acids such as methansulfonic acid and p-toluenesulfonic acid.

In general, the mono-, di-or trisaccharide moiety (i.e., the glycosyl moiety defined by "R") may be attached directly—or thru $(CH_2)_n$ alkylene bridge—to the nitrogen atom of the 1,4-dideoxy-1,4-imino-D-arabinitol moiety thru either an exocyclic or ring carbon atom of the pentose or hexose ring thereby forming a variety of position isomers for each individual glycosyl moiety. Also, similar or dissimilar pentose or hexose moieties may be linked to each other through a glycosidic oxygen bridge wherein the bridging oxygen atom is attached to an exocyclic and/or endocyclic carbon atom of the pentose or hexose moiety of which the glycosyl radical is comprised; again the position isomers, and the optical and geometric isomeric forms thereof, all being contemplated as being within the scope of this invention.

Exemplary of glycosyl radicals contemplated by the "R" designation in Formula I are such monosaccharides as glucosyl, galactosyl, fucosyl, fructosyl, mannosyl, ribosyl, arabinosyl, xylosyl, allosyl, altrosyl, gulosyl, idosyl, talosyl and lyxosyl, such disaccharides as isomaltosyl, trehalosyl, α and β cellobiosyl, maltosyl, and such trisaccharides as maltotriosyl and cellotriosyl. Preferred glycosyl radicals are 6- or 4-glucosyl, 1- or 6-fructosyl, 6- or 4-maltosyl and 6- or 4-isomaltosyl. Ether derivatives are those derivatives wherein the hydroxyl group attached to the anomeric carbon atom is etherified and include the $C_{1-6}$ alkyl derivatives, preferably methyl and aromatic derivatives such as phenyl an benzyl. Acyl derivatives, such as those formed at the anomeric carbon atom by reaction of the free hydroxy radical with alkanoic acids or benzoic acid, are also contemplated even through such acylated moieties may easily be removed from the glycosyl radical. Preferred acyl radicals are those formed with acetic or benzoic acids.

The compounds of the present invention are prepared by methods analogously known in the art. It is preferred to condense an appropriately hydroxy protected 1,4-dideoxy-1,4-imino-D-arabinitol (2) with an appropriately hydroxy protected glycosyl triflate or halide, preferably the iodide. In those instances wherein the 1,4-dideoxy-1,4-imino-D-arabinitol is coupled with a triflate the reaction is effected by refluxing an admixture of equimolar quantities of the reactants in an alcohol- and water-free solvent, preferably a chlorinated solvent such as chloroform, under an inert atmosphere, preferably under nitrogen or argon, for about 1 to 3 days until the reaction is completed. Following standard procedures for the isolation and purification of the reaction products, the protecting groups are removed to obtain the desired product. Debenzylation is readily effected with standard techniques such as catalytic hydrogenation in an appropriate solvent, e.g. ethanol, using a catalyst such as palladium or carbon, or by transfer hydrogenation using cyclohexene and methanol. In those instances wherein esters were utilized (partially or completely) as the hydroxy protecting groups, it is preferred to first remove the ester group by treatment with an alkali alkoxide, e.g. sodium methoxide, in methanol to hydrolyze the esters and then deprotect the benzyl ethers using the foregoing hydrogenation procedures.

In those instances wherein a glycosyl halide is coupled with the 1,4-dideoxy-1,4-imino-D-arabinitol the reaction is effected by heating the appropriately hydroxy protected reactants in dry dimethyl formamide (DMF) or other equivalently functioning solvent, at about 60°–90° C. for about 12 to 36 hours, said heating taking place using excess amounts of a weak base ($K_2CO_3$) or a molecular sieve, preferably using excess molar amounts of the halide (up to three times) relative to the amine.

The foregoing reactions are illustrated by the following reaction schemes A and B.

Reaction Scheme A:

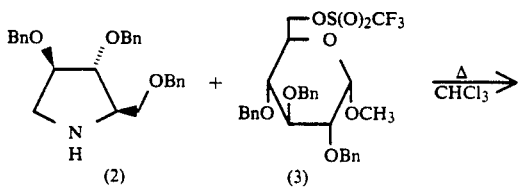

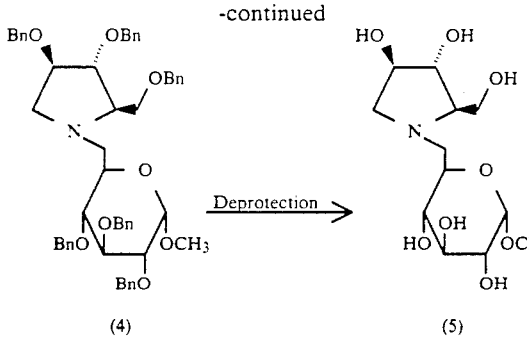

(4) → Deprotection → (5)

Reaction Scheme B:

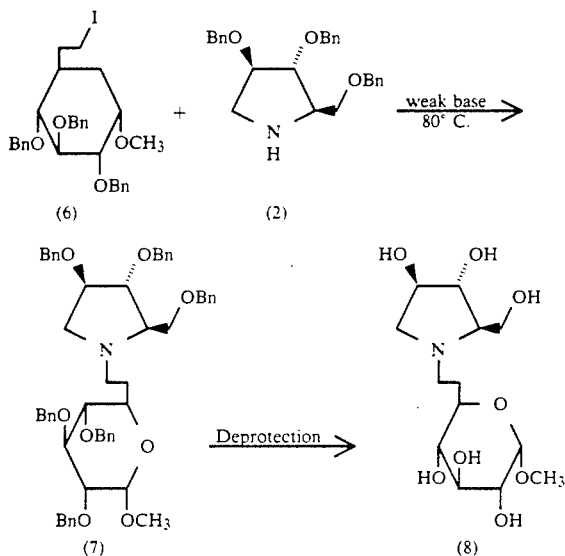

wherein Bn is benzyl.

In its more generic depiction, the following reaction scheme illustrates the processes by which the compounds of formula I may be prepared:

Rection Scheme C:

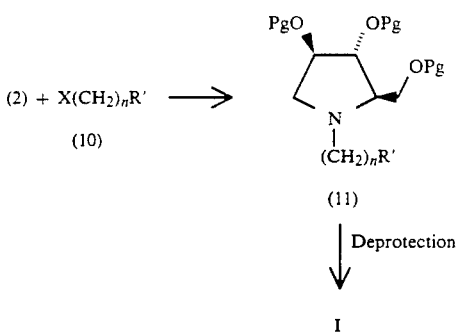

wherein X is a halide or a triflate and R' is a hydroxy-protected glycosyl moiety, Pg is a hydroxy-protecting group, preferably benzyl, and n is zero, 1 or 2.

Appropriately hydroxy protected glycosyl halides (6) and triflates (3) are those glycosyl radicals (as defined in Formula I) wherein the hydroxy group shave been protected with an ester or ether moiety. Preferred esters are the acetate or benzoate esters although other alkanoyl esters, particularly those containing up to six carbon atoms, may be used. The preferred ether is the benzyl ether. Such protected compounds may be prepared by standard procedures very well known and understood in the art; the selection and preparation of the hydroxy-protected intermediates taking into consideration the necessary art for selective deprotection when necessary.

The glycosyl triflates (of which compound 3 is representative) are prepared by standard procedures such as by reaction of a hydroxy-protected glycosyl with tri-fluoro-methylsulfonate anhydride in a chlorinated solvent for about .1-3 hours at about $-78°$ C. to $-10°$ C.

The glycoside halides (of which compound 6 is representative) may be prepared by standard techniques starting with an appropriately hydroxy-protected glycoside bearing one free hydroxy group. In these instances the alcohol is converted to its aldehyde by a Swern oxidation (treatment with oxalyl chloride in dimethylsulfoxide and triethylamine) followed by an in situ conversion of the aldehyde to an olefin by a Wittig reaction (going through a "ylide" prepared from methyltriphenylphosphonium bromide using one equivalent each of n-butyllithium, potassium t-butoxide and t-butanol in tetrahydrofuran at room temperature for about 4 to 8 hours). The olefin is converted to its corresponding alcohol by hydroboration (treatment with boron dimethylsulfide, under nitrogen, followed by oxidation with hydrogen peroxide and sodium hydroxide). The alcohol is mesylated (treatment with mesyl chloride in $CH_2Cl_2$ in excess $NEt_3$ at $-15°$ C. to $0°$ C.) and the mesylate converted to its halide (by treatment in ether at $0°$ C. with magnesium halide), preferably using the iodide.

The following examples illustrate the processes and techniques suitable for the preparation of the compounds of this invention.

EXAMPLE 1

Preparation of Methyl-L-Xylofuranoside

L-xylose (25 g, 0.167 mol) is stirred in methanol (480 mL) along with drierite (11 g) and concentrated sulfuric acid (3.4 mL) during 5 hours at room temperature. The mixture is filtered off and quickly treated by Amberlyst A21 in methanol until neutral pH. The mixture is put to dryness. Flash chromatography on silica gel and elution with a 95:5 mixture of ethyl acetate and methanol yield methyl-L-xylofuranoside in a mixture of anomers as an oil (17.8 g, 65%).

EXAMPLE 2

Preparation of Methyl 2,3,5-Tri-O-Benzyl-L-Xylofuranoside

To a suspension of sodium hydride (14.3 g, 0.36 mol, 60% in mineral oil washed three times with pentane) in a mixture of tetrahydrofuran (125 mL) and dimethylformamide (250 mL) is added dropwise under stirring a mixture of benzylbromide (42.6 mL, 0.36 mol), methyl-L-xylofuranoside (18.96 g, 0.116 mol) and tetra-n-butylammonium iodide (1.86 g) dissolved in tetrahydrofuran (125 mL) and dimethylformamide (250 mL). The mixture is stirred overnight at room temperature. Saturated aqueous ammonium sulfate is added. The mixture is put to dryness under reduced pressure. The residue is taken with water, extracted three times with ethyl acetate. The organic layer is dried over sodium sulfate, filtered and concentrated under reduced pressure to afford an oil. Flash chromatography on silica gel and elution with a 8:2 mixture of cyclohexane and ethyl acetate yield methyl 2,3,5-tri-O-benzyl-L-xylofuranoside in a mixture of anomers as an oil (22.7 g, 45%).

EXAMPLE 3

Preparation of Methyl 2,3,5-Tri-O-Benzyl-L-Xylofuranose

Methyl 2,3,5-tri-O-benzyl-L-xylofuranoside (22.7 g, 56.30 mmol) is dissolved at 0° C. in a 9:1 mixture of trifluoroacetic acid and water (200 mL) and stirred at 0° C. overnight. The mixture is put to dryness under reduced pressure. The oily residue is dissolved in ethyl acetate and washed three times with a saturated solution of sodium bicarbonate. The organic layer is dried over sodium sulfate, filtered and put to dryness under reduced pressure to afford an oil. Flash chromatography on silica gel and elution with a 7:3 mixture of cyclohexane and ethyl acetate yield methyl 2,3,5-tri-O-benzyl-L-xylofuranose as an oil (11.7 g, 53%).

EXAMPLE 4

Preparation of 2,3,5-Tri-O-Benzyl-L-Xylitol

Methyl 2,3,5-tri-O-benzyl-L-xylofuranose (11.7 g, 27.92 mmol) is dissolved in ethanol (150 mL) and sodium borohydride (0.844 g, 30.5 mmol) was added. The mixture is stirred 2 hours at 0° C. The reaction is treated successively by acetone and acetic acid. The mixture is concentrated under reduced pressure. The residue is taken with water, extracted three times with ethyl acetate. The organic layer is dried over sodium sulfate, filtered and concentrated under reduced pressure to afford an oil. Flash chromatography on silica gel and elution with a 1:1 mixture of hexane and ethyl acetate yield 2,3,5-tri-O-benzyl-L-xylitol (10.2 g, 86.5%) as an oil.

EXAMPLE 5

Preparation of 1,4-Di-O-Methanesulfonyl-2,3,5-Tri-O-Benzyl-L-Xylitol 2,3,5-Tri-O-benzyl-L-xylitol (10.2 g, 24.17 nmmol) is dissolved in dry methylene chloride (100 ml) containing triethylamine (10.1 mL, 72.5 mmol). The mixture is cooled to −10° C. and methane sulfonylchloride (3.93 mL, 50.75 mmol) is added dropwise. The mixture is stirred 30 minutes at −10° C. and washed with water. The organic layer is dried over sodium sulfate, filtered and put to dryness under reduced pressure to afford an oil. Flash chromatography on silica gel and elution with a 4:6 mixture of ethyl acetate and cyclohexane yield 1,4-di-O-methanesulfonyl-2,3,5-tri-O-benzyl-L-xylitol as an oil (13.9 g, 99%).

EXAMPLE 6

Preparation of 1-Azido-1-Deoxy-4-O-Methanesulfonyl-2,3,5-Tri-O-Benzyl-L-Xylitol

A mixture of sodium azide (1.72 g, 26.4 mmol) and 1,4-di-O-methanesulfonyl-2,3,5-tri-O-benzyl-L-xylitol (13.9 g, 24 mmol) in dimethylformamide (500 mL) is heated overnight at 60° C. under stirring. Dimethylformamide is evaporated under reduced pressure. The residue is dissolved in ethyl acetate and washed with water. The organic layer is dried over sodium sulfate, filtered and concentrated under reduced pressure, yielding an oil. Flash chromatography on silica gel and elution with a 7:3 mixture of cyclohexane and ethyl acetate yield 1-azido-1-deoxy-4-O-methanesulfonyl-2,3,5-tri-O-benzyl-L-xylitol (8.6 g, 63%) as an oil.

EXAMPLE 7

Preparation of 2,3,5-Tri-O-Benzyl-1,4-Dideoxy-1,4-Imino-D-Arabinitol

1-Azido-1-deoxy-4-O-methanesulfonyl-2,3,5-tri-O-benzyl-L-xylitol (4.5 g, 7.98 mmol) is dissolved in a 1:1 mixture of ethanol and ethyl acetate (30 mL) and Palladium black (0.234 g) is added. The mixture is stirred under hydrogen at atmospheric pressure overnight. The catalyst is filtered off and the solvents evaporated under reduced pressure. Flash chromatography on silica gel and elution with a 95:5 mixture of ethyl acetate and methanol yield 2,3,5-tri-O-benzyl-1,4-dideoxy-1,4-imino-D-arabinitol (2.76 g, 86%) as an oil.

EXAMPLE 8

Methyl 2,3,4-Tri-O-Benzyl-6-O-Trifluoromethylsulfonyl-α-D-Glucopyranoside

To a solution of dry pyridine (0.46 mL) in methylene chloride (17.5 mL) cooled to −15° C. was added trifluoromethanesulfonic anhydride (0.87 mL). The mixture was stirred during 15 min at −10° C., then methyl 2,3,4-tri-O-benzyl-α-D-glucopyranoside (1.2 g, 2.58 mmol) in methylene chloride (5 mL) was added [P. Kovac, V. Sklenar and C. Glaudemans, Carbohydr. Res. 175, 201 (1988)]. The mixture was stirred during 1.5 h at −10° C. The reaction mixture was washed with water. The organic layer was dried over sodium sulfate, filtered and concentrated under reduced pressure to afford an oil. Flash chromatography on silica gel and elution with a 7:3 mixture of hexane and ethyl acetate afforded the expected compound methyl 2,3,4-tri-O-benzyl-6-O-trifluoromethylsulfonyl-α-D-glucopyranoside which was crystallized from hexane (1.43 g, 93%); m.p. 44°–45° C.

EXAMPLE 9

Preparation of 2,3,5-Tri-O-Benzyl-1,4-Dideoxy-1,4-[(2,3,4-Tri-O-Benzyl-6-Deoxy-1-O-Methyl-6-α-D-Glucopyranosyl)Imino]-D-Arabinitol A solution of methyl 2,3,4-tri-O-benzyl-6-O-trifluoromethylsulfonyl-α-D-glucopyranoside (0.928 g, 1.56 mmol) and 2,3,5-tri-O-benzyl-1,4-dideoxy-1,4-imino-D-arabinitol (0.627 g, 1.56 mmol) in ethanol-free chloroform (55 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford an oil. Flash chromatography on silica gel and elution with a 6:4 mixture of hexane and ethyl acetate afforded the expected compound 2,3,5-tri-O-benzyl-1,4-dideoxy-1,4-[(2,3,4-tri-O-benzyl -6-deoxy-1-O-methyl-6-α-D-glucopyranosyl)imino]-D-arabinitol, as a white foam (0.941 g, 71%).

EXAMPLE 10

Preparation of
1,4-Dideoxy-1,4-[(6-Deoxy-1-O-Methyl-6-α-D-Glucopyranosyl)Imino]-D-Arabinitol 2,3,5-tri-O-benzyl-1,4-dideoxy-1,4-[(2,3,4-tri-O-benzyl-6-deoxy-1-O-methyl -6-α-D-glucopyranosyl)imino]-D-arabinitol (0.941 g, 1.11 mmol) was dissolved in a 1:1 mixture of methanol and acetic acid (40 mL) and Pd 10% on charcoal (70 mg) was added. The mixture was stirred under hydrogen at atmospheric pressure during 4 days. The catalyst was filtered off and the solvents were evaporate under reduced pressure. The residue was dissolved in water and passed through a column of Amberlyst A26 OH⊖ form. Lyophilization afforded 1,4-dideoxy-1,4-[(6-deoxy-1-O-methyl-6-α-D-glucopyranosyl) imino]-D-arabinitol as an amorphous solid (0.250 g, 72%).

EXAMPLE 11

Preparation of Methyl
2,3,4-Tri-O-Benzyl-6,7-Dideoxy-α-D-Glucohept-6-Enopyranoside To a solution of oxalyl chloride (1.05 mL, 17.22 mmol) in dry tetrahydrofuran (40 mL) cooled to −78° C., dry dimethyl sulfoxyde (1.3 mL, 18.04 mmol) was added dropwise and then stirred during 35 min at −35° C. The reaction mixture was cooled again to −78° C. and methyl 2,3,4-tri-O-benzyl-α-D-glucopyranoside (6 g, 16.4 mmol) dissolved in tetrahydrofuran (20 mL) was added and the mixture was stirred during 15 min at −35° C., then triethylamine (11.5 mL, 82.65 mmol) was added and the mixture was stirred during 1 h at −35° C. This aldehyde was used without purification and isolation in a wittig reaction described as follows. To dried triphenylmethylphosphonium bromide (11.7 g, 32.8 mmol) suspended in tetrahydrofuran (700 mL) was added dropwise at −78° C. a 1.42M solution of n-butyllithium in hexane (23 mL, 32.66 mmol). The reaction mixture was warmed to room temperature and stirred during 1.5 h. Then the mixture was cooled to 0° C. and potassium tertiobutylate (3.68 g, 32.8 mmol) and dry tertio-butyl alcohol (3 mL, 31.8 mmol) were added. The mixture was stirred again at room temperature during 30 min. The reaction mixture was cooled to −78° C. and the tetrahydrofuran solution of the aldehyde prepared above was added dropwise. The reaction mixture was warmed to room temperature and stirred during 2 h. A saturated aqueous solution of ammonium chloride and the solvents were evaporated under reduced pressure. The residue was dissolved in ether and washed with water. The organic layer was dried over sodium sulfate, filtered and concentrated under reduced pressure to afford a brown oil. Flash chromatography on silica gel and elution with a 4:96 mixture of ethyl acetate and toluene afforded the expected olefine methyl 2,3,4-tri-O-benzyl-6,7-dideoxy-α-D-glucohept-6-enopyranoside (3.26 g, 55%) which crystallized from hexane; m.p. 46°-47° C.

EXAMPLE 12

Preparation of Methyl
2,3,4-Tri-O-Benzyl-6-Deoxy-α-D-Glucoheptopyranoside

To a solution of methyl 2,3,4-tri-O-benzyl-6,7-dideoxy-α-D-glucohept-6-enopyranoside (0.878 g, 2.43 mmol) in dry tetrahydrofuran (5 mL) was added a 10M solution of borane in methyl sulfide (0.24 mL, 2.4 mmol) at 0° C. under nitrogen. The mixture was stirred during 3 h at room temperature. The excess of borane was destroyed with ethanol (1 mL). The mixture was cooled at 0° C. 30% hydrogen peroxyde (0.3 mL) were added. The mixture was refluxed during 2 h. The reaction mixture was diluted with water and extracted three times with ether. The organic layer was dried over sodium sulfate, filtered and concentrated under reduced pressure to afford an oil. Flash chromatography on silica gel and elution with a 1:1 mixture of ethyl acetate and hexane afforded the expected alcohol methyl 2,3,4-tri-O-benzyl-6-deoxy-α-D-glucoheptopyranoside (0.414 g, 45%) which crystallized from hexane; m.p. 50°-53° C.

EXAMPLE 13

Preparation of Methyl
2,3,4-Tri-O-Benzyl-6-Deoxy-7-O-Methylsulfonyl-α-D-Glucoheptopyranoside To a solution of methyl 2,3,4-tri-O-benzyl-6-deoxy-α-D-glucoheptopyranoside (0.35 g, 0.92 mmol) in dry methylene chloride (10 mL) was added triethylamine (0.2 mL, 1.43 mmol). Then the solution was cooled to −10° C. and mesylchloride (0.08 mL), 1 mmol) was added. The mixture was stirred an additional 15 min at −10° C., then the reaction was allowed to warm up to room temperature. The mixture was washed three times with water. The organic phase was dried over sodium sulfate, filtered and concentrated under reduced pressure to afford a yellow oil. Flash chromatography on silica gel and elution with a 40:60 mixture of ethylacetate and hexane afforded the expected mesylate methyl 2,3,4-tri-O-benzyl-6-deoxy-7-O-methylsulfonyl-α-D-glucoheptopyranoside as an oil (0.38 g, 91%).

EXAMPLE 14

Preparation of Methyl
2,3,4-Tri-O-Benzyl-6,7-Dideoxy-7-Iodo-α-D-Glucoheptopyranoside To a solution of methyl 2,3,4-tri-O-benzyl-6-deoxy-7-O-methylsulfonyl-D-glucoheptopyranoside (0.38 g, 0.83 mmol) in ether (5 mL) was added at 0° C. a 0.375M solution of magnesium iodide (6.7 mL). The mixture was stirred 15 min at 0° C. The excess of magnesium iodide was hydrolyzed with water. The reaction mixture was washed with sodium, thiosulfate and water. The organic layer was dried over sodium sulfate, filtered and concentrated under reduced pressure to afford an oil. Flash chromatography on silica gel and elution with a 2:8 mixture of ethyl acetate and hexane afforded the expected iodide methyl 2,3,4-tri-O-benzyl-6,7-dideoxy-7-iodo-α-D-glucoheptopyranoside which was crystallized from hexane (0.368 g, 91%); m.p. 66°-68° C.

EXAMPLE 15

Preparation of
2,3,5-Tri-O-Benzyl-1,4-Dideoxy-1,4-[(2,3,4-Tri-O-Benzyl-6,7-Dideoxy
-1-O-Methyl-7-α-D-Glucoheptopyranosyl)Imino[-D-Arabinitol A solution of methyl 2,3,4-tri-O-benzyl-6,7-dideoxy-7-iodo-α-D-glucoheptopyranoside (0.3 g, 0.51 mmol) and 2,3,5-tri-O-benzyl-1,4-dideoxy-1,4-imino-D-arabinitol (0.069 g, 0.17 mmol) in dry dimethylformamide (3 mL) was heated at 80° C. overnight along with dry potassium carbonate (0.127 g, 0.92 mmol). The dimethylformamide was evaporated under reduced pressure. The residue was taken with ethyl acetate and washed twice with water. The organic layer was dried over sodium sulfate, filtered and concentrated under reduced pressure to afford an oil. Chromatography on neutral alumine activity III and elution with a 8:2 mixture of hexane and ethyl acetate afforded the expected amine 2,3,5-tri-O-benzyl-1,4-dideoxy-1,4-[(2,3,4-tri-O-benzyl -6,7-dideoxy-1-O-methyl-7-α-D-glucoheptopyranosyl)imino]-D-arabinitol as a white foam (0.105 g, 71%).

EXAMPLE 16

Preparation of
1,4Dideoxy-1,4-[(6,7-Dideoxy-1-O-Methyl-7-α-D-Glucoheptopyranosyl)Imino]-D-Arabinitol 2,3,5-tri-O-benzyl-1,4-dideoxy-1,4-[(2,3,4-tri-O-benzyl-6,7-dideoxy-1-O-methyl-7-α-D-glucoheptopyranosyl)imino]-D-arabinitol (0.1 g, 0.116 mmol) was dissolved in acetic acid (15 mL). Palladium 10% on charcoal (0.05 g) was added. The mixture was hydrogenated at 3 atmospheres during two days. The catalyst was removed by filtration and the solvents were evaporated under reduced pressure. The residue was dissolved in water and passed through a column of Amberlyst A26 OH⊖ form. Lyophilisation afforded 1,4-dideoxy-1,4-[(6,7-dideoxy-1-O-methyl-7-α-D-glucoheptopyranosyl) imino]-D-arabinitol (0.03 g, 80% as foam).

EXAMPLE 17

Preparation of
2,3,5-Tri-O-Benzyl-1,4-Dideoxy-1,4-[(1-Deoxy-2,3:4,5-Di-O-Isopropylidene -β-D-Fructopyranosyl)Imino]-L-Arabinitol A solution of 2,3:4,5-di-O-isopropylidene-1-O-trifluoromethylsulfonyl-β-D-fructopyranose (1.17 g, 3.0 mmol) [P. J. Card and W. D. Hitz, J. Amer. Chem. Soc., 106, 5348 (1984)] and 1,4-dideoxy-2,3,5,-tri-O-benzyl-1,4-imino-D-arabinitol (1.209 g, 3.0 mmol) in ethanol-free chloroform (70 ml) was refluxed under nitrogen during 60 h. The mixture was diluted with methylene chloride and washed successively with a saturated aqueous solution bicarbonate and saturated brine. The organic layer was dried over sodium sulfate, filtered and concentrated under reduced pressure to afford an oil flash chromatography on silica gel and elution with graded mixture of hexane and ethyl acetate afforded the expected amine 2,3,5-tri-O-benzyl-1,4-dideoxy-1,4[(1-deoxy-2,3:4,5-di -O-isopropylidene-β-D-fructopyranosyl)imino]-D-arabinitol as an oil (1.6 g, 82.5%).

EXAMPLE 18

Preparation of
2,3,5-Tri-O-Benzyl-1,4-Dideoxy-1,4-[(1-Deoxy-2-O-Methyl-α-D-Fructofuranosyl) Imino]-D-Arabinitol 2,3,5-tri-O-benzyl-1,4-dideoxy-1,4-[(1-deoxy-2,3:4,5-di-O-isopropylidene -β-D-fructopyranosyl)imino]-D-arabinitol (1.4 g, 2.17 mmol) was dissolved in methanol (100 mL) containing 2% of dry hydrochloric acid. The mixture was refluxed during 48 h. The mixture was neutralized with Amberlyst A26 OH⊖ form and filtered. The solvents were evaporated under reduced pressure. Flash chromatography on silica gel and elution with graded mixture of ethyl acetate and methanol afforded the expected amine 2,3,5-tri-O-benzyl-1,4-dideoxy-1,4-[(1-deoxy-2-O-methyl-α-D-Fructofuranosyl)-imino]-D-arabinitol (0.750 g, 60%).

EXAMPLE 19

Preparation of
1,4-Dideoxy-1,4-[(1-Deoxy-2-O-Methyl-α-D-Fructofuranosyl)Imino-D-Arabinitol The amine 2,3,5-tri-O-benzyl-1,4-dideoxy-1,4-[(1-deoxy-2-O-methyl-α-D-fructofuranosyl) imino]-D-arabinitol (0.550 g, 0.949 mmol) was dissolved in acetic acid (25 mL), palladium 10% on charcoal (0.3 g) was added. The mixture was hydrogenated during 3 days at 3 bars. The catalyst was removed by filtration and the solvents were evaporated under reduced pressure. The residue was dissolved in water and neutralized with Amberlyst A26 OH⊖ form and filtered. The mixture was put to dryness under reduced pressure. Flash chromatography on silica gel and elution with graded mixture of chloroform, methanol and water afforded the expected amine 1,4-dideoxy-1,4-[(deoxy-2-O-methyl-α-D-fructofuranosyl)imino]-D-arabinitol as an amorphous solid (0.23 g, 78%).

EXAMPLE 20

Preparation of Methyl
2,3,6-Tri-O-Benzyl-4-O-Trifluoromethylsulfonyl-α-D-Galactopyranoside To a solution of dry pyridine (0.46 mL) in methylene chloride (17.5 mL) cooled to −15° C. was added trifluoromethane sulfonic anhydride (0.87 mL). The mixture was stirred during 15 min at −10° C., then methyl 2,3,6-tri-O-benzyl-α-D-galactopyranoside (1.2 g, 2.58 mmol) in methylene chloride (5 mL) was added (N. Morishima, S. Koto, M. Oshima, A. Sugimoto and S. Zen, Bull. Chem. Soc. Jpn, 56, 2849 (1983)). The mixture was washed with water. The organic layer was dried over sodium sulfate, filtered and concentrated under reduced pressure to afford an oil which was the expected triflate methyl 2,3,6-tri-O-benzyl-4-O-trifluoromethyl-sulfonyl-α-D -galactopyranoside (1.43 g, 93%).

EXAMPLE 21

Preparation of
2,3,5-Tri-O-Benzyl-1,4-dideoxy-1,4-[(2,3,6-Tri-O-Benzyl-4-Deoxy-1-O-Methyl -4-α-D-Glucpyranosyl)Imino]-D-Arabinitol A solution of methyl 2,3,6-tri-O-benzyl-4-O-trifluoromethylfulfonyl-α-D-galactopyranoside (1.46 g, 2.97 mmol) and 2,3,5-tri-O-benzyl-1,4-dideoxy-1,4-imino-D-arabinitol (1.2 g, 2.97 mmol) in ethanol-free chloroform (70 mL) was refluxed under nitrogen during 3 days. The mixture was diluted with methylene chloride and washed successively with a saturated aqueous solution of sodium bicarbonate and saturated brine. The organic layer was dried over sodium sulfate, filtered and concentrated under reduced pressure to afford an oil. Flash chromatography on silica gel and elution with graded mixtures of hexane and ethyl acetate afforded the expected amine 2,3,5-tri-O-benzyl-1,4-dideoxy-1,4-[(2,3,6-tri -O-benzyl-4-deoxy-1-O-methyl-4-α-D-glucopyranosyl)imino]-D-arabinitol as an oil (0.75 g, 30%).

EXAMPLE 22

Preparation of
1,4-Dideoxy-1,4-[(4-Deoxy-1-O-Methyl-4-α-D-Glucopyranosyl)Imino]-D-Arabinitol The amine 2,3,5-tri-O-benzyl-1,4-dideoxy-1,4-[(2,3,6-tri-O-benzyl-4-deoxy-1-O-methyl-α-D-glucopyranosyl)imino]-D-arabinitol (0.7 g, 0.82 mmol) was dissolved in acetic acid (20 mL). Palladium 10% on charcoal (0.5 g) was added. The mixture was hydrogenated during 4 days at 3 bars. The catalyst was filtered. The solvents were evaporated under reduced pressure. The residue was dissolved in water and neutralized with Amberlyst A26 OH⊖ form. The mixture was filtered and the aqueous layer was put to dryness under reduced pressure to afford a foam. Flash chromatography on silica gel and elution with a 50:50:4 mixture of methanol, chloroform and water afforded the expected amine 1,4-dideoxy-1,4-[(4-deoxy-1-O-methyl-4-α-D-glucopyranosyl) imino]-D-arabinitol as a foam (0.783 g, 72%).

EXAMPLE 23

Preparation of Methyl 2,3,4-Tri-O-Benzyl-6-O-(2,3,4-Tri-O-Benzyl-6-O-Tri-Fluoromethylsulfonyl -α-D-Glucopyranosyl-α-D-Glucopyranoside To a solution of dry pyridine (0.24 mL) in methylene chloride (25 mL) cooled to −15° C. was added trifluoromethane sulfonic anhydride (0.45 mL). The mixture was stirred during 15 min at −10° C., then methyl 6-O-(2,3,4-tri-O-benzyl-α-D-glucopyranosyl)-2,3,4-tri-O-benzyl -α-D-glucopyranoside (1.2 g, 1.34 mmol) in methylene chloride (5 mL) was added (R. Eby and C. Schuerch, Carbohydr. Res., 50, 203 (1976)). The mixture was stirred during 1.5 h at −10° C. The reaction mixture was washed with water. The organic layer was dried over sodium sulfate, filtered and concentrated under reduced pressure to afford an oil (1.35 g, 98%), which was the expected triflate methyl 2,3,4-tri-O-benzyl-6-O-(2,3,4-tri-O-benzyl-6-O-trifluoromethylsulfonyl-α-D-glucopyranosyl)-α-D-glucopyranoside.

EXAMPLE 24

Preparation of
2,3,5-Tri-O-Benzyl-1,4-Dideoxy-N-[2,3,4-Tri-O-Benzyl-6-Deoxy-1-(2,3,4-Tri -O-Benzyl-1-O-Methyl-6-O-α-D-Glucopyranosyl)-α-D-Glucopyranosyl]-1,4-Imino-D-Arabinitol A solution of methyl 2,3,4-tri-O-benzyl-6-O-(2,3,4-tri-O-benzyl-6-O-trifluoromethylsulfonyl -α-D-glucopyranosyl)-α-D-glucopyranoside (1.3 g, 1.26 mmol) and 2,3,5-tri-O-benzyl-1,4-dideoxy-1,4-imino-D-arabinitol (0.509 g, 1.26 mmol) in ethanol-free chloroform (50 mL) was refluxed under nitrogen during 48 h. The mixture was diluted with methylene chloride and washed successively with a saturated aqueous solution of sodium bicarbonate and saturated brine. The organic layer was dried over sodium sulfate, filtered and concentrated under reduced pressure to afford a foam. Flash chromatography on silica gel and elution with graded mixture of hexane and ethyl acetate afforded the expected amine 2,3,5-tri-O-benzyl-1,4-dideoxy-N-[2,3,4-tri-O-benzyl-6-deoxy-1-(2,3,4-tri-O-benzyl-1-O-benzyl-1-O-methyl-6O-α-D-glucopyranosyl) -α-D-glucopyranosyl]-1,4-imino-D-arabinitol (1.24 g, 75%) as a foam.

EXAMPLE 25

Preparation of
1,4-Dideoxy-N-[6-Deoxy-1-(1-O-Methyl-6-O-α-D-Glucopyranosyl) -α-D-Glucopyranosyl]-1,4-Imino-D-Arabinitol The amine 2,3,5-tri-O-benzyl-1,4-dideoxy-N-[2,3,4-tri-O-benzyl-6-deoxy-1-(2,3,4-tri-O-benzyl-1-O-methyl-6-O-α-D-glucopyranosyl)-α-D-glucopyranosyl]-1,4-imino-D-arabinitol (1.2 g, 0.937 mmol) was dissolved in acetic acid (30 mL). Palladium 20% on charcoal (0.5 g) was added. The mixture was hydrogenated during 4 days at 3 atmosphere. The catalyst was removed by filtration and the solvents were evaporated under reduced pressure. Flash chromatography on silica gel and elution with graded mixture of chloroform, methanol and water afforded the expected amine 1,4-dideoxy-N-[6-deoxy-1-(1-O-methyl-6-O-α-D-glucopyranosyl) -α-D-glucopyranosyl]-1,4-imino-D-arabinitol (0.310 g, 70%) as a foam.

EXAMPLE 26

Preparation of Methyl
6-O-(2,3,4-Tri-O-Benzyl-6,7-Dideoxy-α-D-Glucohept-6-Enopyranosyl) -2,3,4-Tri-O-Benzyl-α-D-Glucopyranoside To a solution of oxalyl chloride (0.37 mL, 5.97 mmol) in dry tetrahydrofuran (40 mL) cooled to −78° C., dry dimethyl sulfoxyde (0.45 mL), 6.26 mmol) was added dropwise and then stirred during 35 min at −35° C. The reaction mixture was cooled again to −78° C. and methyl 6-O-(2,3,4-tri-O-benzyl-α-D-glucopyranosyl)-2,3,4-tri-O-benzyl-α-D -glucopyranoside (5.1 g, 5.69 mmol) dissolved in tetrahydrofuran (20 mL) was added and the mixture was stirred during 15 min at −35° C., then triethylamine (3.96 mL, 28.45 mmol) was added and the mixture was stirred during 1 h at −35° C. This aldehyde was used without purification and isolation in a Wittig reaction described as follows. To dried triphenylmethylphosphonium bromide (4.059 g, 11.38 mmol) suspended in tetrahydrofuran (100 mL) was added dropwise at −78° C. a 1.55M solution of n-butyllithium in hexane (7.34 mL, 11.38 mmol). The reaction mixture was warmed to room temperature and stirred during 1.5 h. Then the mixture was cooled to 0° C. and potassium tertio-butylate (1.275 g, 11.38 mmol) and dry tertio-butyl alcohol (1.04 mL, 11.38 mmol) were added. The mixture was stirred again at room temperature during 30 min. The reaction mixture was cooled to −78° C. and the tetrahydrofuran solution of the aldehyde prepared above was added dropwise. The reaction mixture was warmed to room temperature and stirred during 2 h. A saturated aqueous solution of ammonium chloride and the solvents were evaporated under reduced pressure. The residue was dissolved in ethyl acetate and washed with water. The organic layer was dried over sodium sulfate, filtered and concentrated under reduced pressure to afford a brown oil. Flash chromatography on silica gel and elution with a graded mixture of carbon tetrachloride and ethyl acetate afforded the expected olefine methyl 6-O-(2,3,4-tri-O-benzyl-6,7-dideoxy -α-D-glucohept-6-enopyranosyl)-2,3,4-tri-O-benzyl-α-D-glucopyranoside (2.54 g, 50%) as an amorphous solid.

EXAMPLE 27

Preparation of Methyl
6-O-(2,3,4-Tri-O-Benzyl-6-Deoxy-α-D-Glucoheptopyranosyl)
-2,3,4-Tri-O-Benzyl-α-D-Glucopyranoside To a solution of methyl 6-O-(2,3,4-tri-O-benzyl-6,7-dideoxy-α-D-glucohept-6-enopyranosyl) -2,3,4-tri-O-benzyl-α-D-glucopyranoside (2.54 g, 2.85 mmol) in dry tetrahydrofuran (10 mL) was added a 10M solution of borane in methyl sulfide (0.28 mL, 2.8 mmol) at 0° C. under nitrogen. The mixture was stirred during 3 h at room temperature. Then the mixture was cooled to 0° C. The excess of borane was destroyed with ethanol (1 mL). The mixture was cooled at 0° C. 30% hydrogen peroxyde (0.3 mL) and 3N aqueous solution of sodium hydroxyde (0.3 mL) were added. The mixture was refluxed during 2 h. The reaction mixture was diluted with water and extracted three times with ethyl acetate. The organic layer was dried over sodium sulfate, filtered and concentrated under reduced pressure to afford a foam. Flash chromatography on silica gel and elution with a graded mixture of carbon tetrachloride and ethyl acetate afforded the expected alcohol methyl 6-O-(2,3,4-tri-O-benzyl-6-deoxy-α-D-glucoheptopyranosyl) -2,3,4-tri-O-benzyl-α-D-glucopyranoside (1.245 g, 48%) as a foam.

EXAMPLE 28

Preparation of Methyl
6-O-(2,3,4-Tri-O-Benzyl-6,7-Dideoxy-7-Iodo-α-D-Glucoheptopyranosyl)
-2,3,4-Tri-O-Benzyl-α-D-Glucopyranoside To a solution of methyl 6-O-(2,3,4-tri-O-benzyl-6-deoxy-α-D-glucoheptopyranosyl) -2,3,4-tri-O-benzyl-α-D-glucopyranoside (1.245 g, 1.37 mmol) in dry methylene chloride (15 mL) was added triethylamine (0.29 mL, 2.05 mmol). Then the solution was cooled to −10° C., and mesylchloride (0.11 mL, 1.42 mmol) was added dropwise. The mixture was stirred an additional 15 min at −10° C., then the reaction mixture was washed three times with water. The organic layer was dried over sodium sulfate, filtered and concentrated under reduced pressure to afford a foam which was used without further purification. The crude methyl 6-O-(2,3,4-tri-O-benzyl-6-deoxy-7-O-methylsulfonyl-α-D-glucoheptopyranosyl) -2,3,4-tri-O-benzyl-α-D-glucopyranoside was dissolved in ether (20 mL). To this mixture a 0.35M solution of magnesium iodide in ether (17.5 mL) was added dropwise at 0° C. The excess of magnesium iodide was hydrolyzed with water. The reaction mixture was washed with sodium, thiosulfate and water. The organic layer was dried over sodium sulfate, filtered and concentrated under reduced pressure to afford a foam. Flash chromatography on silica gel and elution with a graded mixture of carbon tetrachloride and ethyl acetate afforded the expected iodide methyl 6-O-(2,3,4-tri-O-benzyl-6,7-dideoxy-7-iodo -α-D-glucoheptopyranosyl)-2,3,4-tri-O-benzyl-α-D-glucopyranoside (1.145 g, 82%) as a foam.

EXAMPLE 29

Preparation of
2,3,5-Tri-O-Benzyl-1,4-Dideoxy-N-[2,3,4-Tri-O-Benzyl-6,7-Dideoxy
-1-(2,3,4-Tri-O-Benzyl-1-O-Methyl-6-O-α-D-Glucopyranosyl)
-α-D-Glucoheptopyranosyl]-1,4-Imino-D-Arabinitol A solution of the iodide methyl 6-O-(2,3,4-tri-O-benzyl-6,7-dideoxy-7-iodo -α-D-glucoheptopyranosyl)-2,3,4-tri-O-benzyl-α-D-glucopyranoside (1.1 g, 1.08 mmol) and the amine 2,3,5-tri-O-benzyl-1,4-dideoxy-1,4-imino -D-arabinitol (0.145 g, 0.36 mmol) in dry dimethlformamide (4 mL) was heated at 80° C. overnight along with dry potassium carbonate (0.206 g, 1.49 mmol). The dimethylformamide was evaporated under reduced pressure. The residue was taken with ethyl acetate and washed twice with water. The organic layer was dried over sodium sulfate, filtered and concentrated under reduced pressure to afford a foam. Chromatography on neutral aluminum oxyde activity III and elution with a graded mixture of carbon tetrachloride and ethyl acetate afforded the expected amine 2,3,5-tri-O-benzyl-1,4-dideoxy-N-[2,3,4-tri-O-benzyl-6,7-dideoxy-1-(2,3,4-tri -O-benzyl-1-O-methyl-6-O-α-D-glucopyranosyl)-α-D-glucoheptopyranosyl]-1,4-imino-D-arabinitol (0.326 g, 70%) as a foam.

EXAMPLE 30

Preparation of
1,4-Dideoxy-N-[6,7-Dideoxy-1-(1-O-Methyl-6-O-α-D-Glucopyranosyl)
-α-D-Glucoheptopyranosyl]-1,4-Imino-D-Arabinitol The amine 2,3,5-tri-O-benzyl-1,4-dideoxy-N-[2,3,4-tri-O-benzyl-6,7-dideoxy-1-(2,3,4-tri-O-benzyl-1-O-methyl-6-O-α-D-glucopyranosyl) -α-D-glucoheptopyranosyl]-1,4-imino-D-arabinitol (0.30 g, 0.231 mmol) was dissolved in acetic acid (30 mL). Palladium 10% on charcoal (0.4 g) was added. The mixture was hydrogenated during 4 days at 3 atmospheres. The catalyst was removed by filtration and the solvents were evaporated under reduced pressure. The residue was dissolved in water and passed through a column of Amberlyst A26 OH⊖. Water was evaporated under reduced pressure. Flash chromatography on silica gel and elution with a graded mixture of chloroform, methanol and water afforded the expected amine 1,4-dideoxy-N-[6,7-dideoxy-1-(1-O-methyl -6-O-α-D-glucopyranosyl)-α-D-glucoheptopyranosyl]-1,4-imino-D-arabinitol (0.076 g, 68%) as an amorphous solid.

EXAMPLE 31

Preparation of Methyl
2,3,6-Tri-O-Benzyl-4-Cyano-4-Deoxy-α-D-Glucopyranoside

A solution of methyl 2,3,6-tri-O-benzyl-4-O-trifluoromethylsulfonyl-α-D-galactopyranoside (3 g, 6.07 mmol) and tetra-n-butyl ammonium cyanide (6.51 g, 24.28 mmol) in ethanol-free chloroform (60 mL) was refluxed under nitrogen during 24 h. The reaction mixture was diluted with methylene chloride, washed twice with water. The organic layer was dried over sodium sulfate, filtered and concentrated under reduced pressure to afford an oil. Flash chromatography on silica gel and elution with a graded mixture of hexane and ethyl acetate afforded the expected nitrile methyl 2,3,6-tri-O- benzyl-4-cyano-4-deoxy-α-D-glucopyranoside (1.75 g, 61%) as an oil.

EXAMPLE 32

Preparation of Methyl 2,3,6-Tri-O-Benzyl-4-Deoxy-4-Formyl-α-D-Gluco-Pyranoside To a solution of methyl 2,3,6-tri-O-benzyl-4-cyano-4-deoxy-α-D-glucopyranoside (1.75 g, 3.7 mmol) in dry tetrahydrofuran (10 mL) was added dropwise at −78° C. a 1.2M solution of diisobutyl aluminum hydride in n-hexane (3.1 mL). The mixture was stirred under argon at −78° C. during 3 h. Methanol (2 mL) was added and the mixture was warmed to 0° C. Then the solvents were evaporated under reduced pressure. Ether (50 mL) and 0.1N aqueous hydrochloric acid (40 mL) were added, the mixture was stirred at 0° C. during 1 h. Then after decantation the organic layer was dried over sodium sulfate, filtered and concentrated under reduced pressure to afford the expected aldehyde methyl 2,3,6-tri-O-benzyl-4-deoxy-4-formyl-α-D-glucopyranoside as an oil (1.7 g, 96%) which was used without purification.

EXAMPLE 33

Preparation of Methyl 2,3,6-Tri-O-Benzyl-4-Deoxy-4-Hydroxymethyl-α-D-Glucopyranoside The aldehyde methyl 2,3,6-tri-O-benzyl-4-deoxy-4-hydroxymethyl-α-D-glucopyranoside (1.7 g, 3.57 mmol) was dissolved in ethanol (15 mL). The mixture was cooled to 0° C. and solid sodium borohydride (0.068 g, 1.8 mmol) was added portionwise. The mixture was stirred 1 h at 0° C. Then acetic acid (0.4 mL) was added and the solvents were evaporated under reduced pressure. The residue was taken with ethyl acetate and washed with saturated aqueous sodium bicarbonate and saturated brine. The organic layer was dried over sodium sulfate, filtered and concentrated under reduced pressure to afford an oil. Flash chromatography over silica gel and elution with a graded mixture of hexane and ethyl acetate afforded the expected alcohol methyl 2,3,6-tri-O-benzyl-4-deoxy-4-hydroxymethyl-α-D-glucopyranoside as an oil (1.19 g, 70%).

EXAMPLE 34

Preparation of Methyl 2,3,6-Tri-O-Benzyl-4-Deoxy-4-Trifluoromethylsulfonyloxymethyl-α-D-Glucopyranoside To a solution of dry pyridine (0.45 mL) in methylene chloride (30 mL) cooled to −15° C. was added trifluoromethanesulfonic anhydride (0.84 mL). The mixture was stirred during 15 min at −10° C., then methyl 2,3,6-tri-O-benzyl-4-deoxy-4-trifluoromethylsulfonyloxymethyl -α-D-glucopyranoside (1.19 g, 2.49 mmol) in methylene chloride (5 mL) was added. The mixture was stirred during 1.5 h at −10° C. The reaction mixture was washed with water. The organic layer was dried over sodium sulfate, filtered and concentrated under reduced pressure to afford an oil (1.443 g, 95%) which was the expected triflate methyl 2,3,6-tri-O-benzyl-4-deoxy-4-trifluoromethylsulfonyloxymethyl-α-D-glucopyranoside.

EXAMPLE 35

Preparation of 2,3,5-Tri-O-Benzyl-1,4-Dideoxy-1,4-[(2,3,6-Tri-O-Benzyl-4-Deoxy-1-O-Methyl-4-α-D-Glucopyranosyl)Methylimino]-D-Arabinitol A solution of methyl 2,3,6-tri-O-benzyl-4-deoxy-4-trifluoromethylsulfonyloxymethyl -α-D-glucopyranoside (1 g, 1.64 mmol) and 2,3,5-tri-O-benzyl-1,4-dideoxy-1,4-imino-D-arabinitol (0.66 g, 1.64 mmol) in ethanol-free chloroform (60 mL) was refluxed under nitrogen during 48 h. The mixture was diluted with methylene chloride and washed successively with a saturated aqueous solution of sodium bicarbonate and saturated brine. The organic layer was dried over sodium sulfate, filtered and concentrated under reduced pressure to afford a foam. Flash chromatography on silica gel and elution with a graded mixture of hexane and ethyl acetate afforded the expected amine 2,3,5-tri-O-benzyl-1,4-dideoxy-1,4-[(2,3,6-tri-O-benzyl-4-deoxy -1-O-methyl-4-α-D-glucopyranosyl)methylimino]-D-arabinitol (0.979 g, 70%) as a foam.

EXAMPLE 36

Preparation of 1,4-Dideoxy-1,4-[(4-Deoxy-1-O-Methyl-4-α-D-Glucopyranosyl) Methylimino]-D-Arabinitol The amine 2,3,6-tri-O-benzyl-1,5-dideoxy-1,5-[(2,3,6-tri-O-benzyl-4-deoxy -1-O-methyl-4-α-D-glucopyranosyl)methyl-imino]-D-arabinitol (0.98 g, 1.13 mmol) was dissolve din acetic acid (20 mL). Palladium 10% on charcoal (0.8 g) was added and the mixture was hydrogenated during 3 days at 3 bars. The catalyst was removed by filtration and the solvents were evaporated under reduced pressure. Flash chromatography on silica gel and elution with a graded mixture of chloroform, methanol and water afforded the expected amine 1,4-dideoxy-1,4-[(4-deoxy-1-O-methyl-4-α-D-glucopyranosyl) methylimino]-D-arabinitol (0.262 g, 72%) as an amorphous solid.

EXAMPLE 37

Preparation of 2,3,6-Tri-O-Benzyl-D-Galactopyranose

Methyl 2,3,6-tri-O-benzyl-α-D-galactopyranoside (5 g, 10.775 mmol) was dissolved at 0° C. in a 9:1 mixture of trifluoroacetic acid and water (50 mL) [N. Morishima, S. Koto, M. Oshima, A. Sugimoto and S. Zen, Bull Chem. Soc. Jpn 56, 2849 (1983)]. The mixture was stirred overnight at 0° C. The solvents were evaporated under reduced pressure without heating. The residue was dissolved in ethyl acetate and washed successively with sodium bi-carbonate and brine. The organic layer was dried over sodium sulfate, filtered and concentrated under reduced pressure to afford an oil. Flash chromatography on silica gel and elution with a graded mixture of ethyl acetate and hexane afforded 2,3,6-tri-O-benzyl-D-galactopyranose (3.927 g, 81%) as an oil.

EXAMPLE 38

Preparation of 1,4-Di-O-Acetyl-2,3,6-Tri-O-Benzyl-D-Galactopyranose 2,3,6-tri-O-benzyl-D-galactopyranose (3.927 g, 8.72 mmol) was dissolved in dry pyridine (25 mL) and acetic anhydride (5 mL) was added. The mixture was stirred during 24 h at room temperature. The solvent was evaporated under high vacuum. The residue was dissolved in ethyl acetate and washed with water. The organic layer was dried over sodium sulfate, filtered and concentrated under reduced pressure to afford the expected diacetate 1,4-di-O-acetyl-2,3,6-tri-O-benzyl-D-galactopyranose (4.64 g, 99%) as an oil which was used without purification.

EXAMPLE 39

Preparation of 4-O-Acetyl-2,3,6-Tri-O-Benzyl-α-D-Galactopyranosyl Chloride

A solution of 1,4-di-O-acetyl-2,3,6-tri-O-benzyl-D-galactopyranose (4.64 g, 8.67 mmol) in ether (10 mL) was treated with ethereal hydrogen chloride (0.2 g/mL, 25 mL). The mixture was stirred at room temperature during 48 h. The solvents were evaporated under reduced pressure to afford an oil. Flash chromatography on silica gel and elution with a graded mixture of carbon tetrachloride and ethyl acetate afforded 4-O-acetyl-2,3,6-tri-O-benzyl-α-D-galactopyranosyl chloride (3.142 g, 71%) as an oil.

EXAMPLE 40

Preparation of Methyl 4-O-(4-O-Acetyl-2,3,6-Tri-O-Benzyl-α-D-Galactopyranosyl)-2,3,6-Tri -O-Benzyl-α-D-Glucopyranoside Ethereal silver perchlorate (0.08M, 84.5 mL, 6.76 mmol) was added with stirring at −30° C. to a solution of methyl-2,3,6-tri-O-benzyl -α-D-glucopyranoside (2.284 g, 4.93 mmol) [P. J. Garegg, H. Hultberg and S. Wallin, Carbohydr. Res., 108, 97 (1982)], 4-O-acetyl-2,3,6-tri-O-benzyl-α-D-galactopyranosyl chloride (3.142 g, 6.154 mmol) and 2,4,6-trimethylpyridine (0.89 mL, 6.76 mmol) in ether (20 mL). The mixture was stirred 15 min at −30° C. and silver chloride precipitated. The mixture was filtered through a celite pad, the solids were washed with ether, the filtrate was concentrated under reduced pressure. The residue was dissolved in methylene chloride and the organic layer was washed successively with aqueous sodium thiosulfate and water. The organic layer was dried over sodium sulfate, filtered and concentrated under reduced pressure to afford a foam. Flash chromatography on silica gel and elution with a graded mixture of hexane and ethyl acetate afforded methyl 4-O-(4-O-acetyl-2,3,6-tri-O-benzyl -α-D-galactopyranosyl)-2,3,6-tri-O-benzyl-α-D-glucopyranoside (2.543 g, 55%) as a foam.

EXAMPLE 41

Preparation of Methyl 2,3,6-Tri-O-Benzyl-4-O-(2,3,6-Tri-O-Benzyl-α-D-Galactopyranosyl) -α-D-Glucopyranoside Methyl 4-O-(4-O-acetyl-2,3,6-tri-O-benzyl-α-D-galactopyranosyl)-2,3,6-tri -O-benzyl-α-D-glucopyranoside (2.543 g, 2.71 mmol) was dissolved in hot toluene (20 mL) and methanol (80 mL) was added, followed by a few drops of 1M. methanolic sodium methoxide. The mixture was stirred at room temperature during 2 h. The reaction mixture was made neutral with Amberlite IR 120 (H+) resin, filtered and concentrated under reduced pressure to afford methyl 2,3,6-tri-O-benzyl-4-O-(2,3,6-tri-O-benzyl -α-D-galactopyranosyl)-α-D-glucopyranoside (2.42 g, 100%) as an amorphous solid.

EXAMPLE 42

Preparation of Methyl 4-O-(2,3,6-Tri-O-Benzyl-4-O-Trifluoromethylsulfonyl-α-D-Galactopyranosyl) -2,3,6-Tri-O-Benzyl-α-D-Glucopyranoside To a solution of dry pyridine (0.49 mL) in dry methylene chloride (40 mL) cooled to −15° C. was added trifluoromethanesulfonic anhydride (0.91 mL). The mixture was stirred during 15 min at −10° C., then methyl 2,3,6-tri-O-benzyl-4-O-(2,3,6-tri-O-benzyl -α-D-galactopyranosyl)-α-D-glucopyranoside (2.428 g, 2.71 mmol) in methylene chloride (10 mL) was added. The mixture was stirred during 1.5 h at −10° C. The reaction mixture was washed with water. The organic layer was dried over sodium sulfate, filtered and concentrated under reduced pressure to afford an oil (2.702 g, 97%) which was the expected triflate methyl 4-O-(2,3,6-tri-O-benzyl-4-O-trifluoromethylsulfonyl-α-D-galactopyranosyl) -2,3,6-tri-O-benzyl-α-D-glucopyranoside.

EXAMPLE 43

Preparation of 2,3,5-Tri-O-Benzyl-1,4-Dideoxy-N-[2,3,6-Tri-O-Benzyl-4-Deoxy-1-(2,3,6-Tri -O-Benxyl-1-O-Methyl-4-O-α-D-Glucopyranosyl)-α-D-Glucopyranosyl]-1-4-Imino-D-Arabinitol A solution of methyl 4-O-(2,3,6-tri-O-benzyl-4-O-trifluoromethysulfonyl-α-D-galactopyranosyl)-2,3,6-tri-O-benzyl-α-D-glucopyranoside (1.30 g, 1.25 mmol) and 2,3,5-tri-O-benzyl-1,4-dideoxy-1,4-imino-D-arabinitol (0.5 g, 1.25 mmol) in ethanol-free chloroform (50 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford a foam. Flash chromatography on silica gel and elution with a graded mixture of hexane and ethyl acetate afforded the expected amine 2,3,5-tri-O-benzyl-1,4-dideoxy-N-[2,3,6-tri-O-benzyl-4-deoxy-1-(2,3,6-tri-O-benzyl-1-O-methyl-4-O-α-D-gluco-pyranosyl)-α-D-glucopyranosyl]-1,4-imino-D-arabinitol (1.1 g, 68%) as an amorphous solid.

EXAMPLE 44

Preparation of 1,4-Dideoxy-N-[4-Deoxy-1-(1-O-Methyl-4-O-α-D-Glucopyranosyl) -α-D-Glucopyranosyl]-1,4-Imino-D-Arabinitol 2,3,5-tri-O-benzyl-1,4-dideoxy-N-[2,3,6-tri-O-benzyl-4-deoxy-1-(2,3,6-tri -O-benzyl-1-O-methyl-4-O-α-D-glucopyranosyl)-α-D-glucopyranosyl]-1,4-imino-D-arabinitol (1 g, 0.78 mmol) was dissolved in acetic acid (30 mL). Palladium 10% on charcoal (0.5 g) was added. The mixture was hydrogenated during 4 days at 3 atmospheres. The catalyst was removed by filtration and the solvents were evaporated under reduced pressure. The residue was taken with water and passed through a column of Amberlyst A26 OH⊖ from. Water was evaporated under reduced pressure and flash chromatography on silica gel and elution with a graded mixture of chloroform, methanol and water afforded the expected amine 1,4-dideoxy-N-[4-deoxy-1-(1-O-methy-4-

O-α-D-glucopyranosyl)  -β-D-glucopyranosyl]-1,4-imino-D-arabinitol (0.257 g, 70%) as an amorphous solid.

EXAMPLE 45

Preparation of 1-Ethenyl-1,2:3,4-Di-O-Isopropylidene-β-D-Arabinopyranose

To a solution of oxalyl chloride (1.05 mL, 17.22 mmol) in dry tetrahydrofuran (40 mL) cooled to −78° C., dry dimethyl sulfoxyde (1.3 mL, 18.04 mmol) was added dropwise and then stirred during 35 min at −35° C. The reaction mixture was cooled again to −78° C. and 2,3:4,5-di-O-isopropylidene-D-fructopyranose (4.26 g, 16.4 mmol) [R. F. Brady, Carbohydr. Res., 15, 35 (1970)] dissolved in tetrahydrofuran (20 mL) was added and the mixture was stirred during 15 min at −35° C., then triethylamine (11.5 mL, 82.65 mmol) was added and the mixture was stirred during 1 h at −35° C. This aldehyde was used without purification and isolation in a Wittig reaction described as follows. To dried triphenyl-methylphosphonium bromide (11.7 g, 32.8 mmol) suspended in tetrahydrofuran (400 mL) was added dropwise at −78° C. a 1.55M solution of n-butyllithium in hexane (21 mL, 32.66 mmol). The reaction mixture was warmed to room temperature and stirred during 1.5 h. Then the mixture was cooled to 0° C. and potassium tertio-butylate (3.68 g, 32.8 mmol) and dry tertio-butyl alcohol (3 mL, 31.8 mmol) were added. The mixture was stirred again at room temperature during 30 min. The reaction mixture was cooled to −78° C. and the tetrahydrofuran solution of the aldehyde prepared above was added dropwise. The reaction mixture was warmed to room temperature and stirred during 2 h. A saturated aqueous solution of ammonium chloride and the solvents were evaporated under reduced pressure. The residue was dissolved in ether and washed with water. The organic layer was dried over sodium sulfate, filtered and concentrated under reduced pressure to afford a brown oil. Flash chromatography on silica gel and elution with a graded mixture of hexane and ethyl acetate afforded the expected olefin 1-ethenyl-1,2:3,4-di-O-isopropylidene-β-D-arabinopyranose (2.77 g, 66%) as an oil.

EXAMPLE 46

Preparation of 1,2,3,4-Di-O-Isopropylidene-1-(2-Hydroxyethyl)-β-D-Arabinopyranose To a solution of 1-ethenyl-1,2:3,4-di-O-isopropylidene-β-D-arabinopyranose (2 g, 7.81 mmol) in dry tetrahydrofuran (15 mL) was added a 10M solution of borane in methyl sulfide (0.78 mL, 7.8 mmol) at 0° C. under nitrogen. The mixture was stirred during 3 h at room temperature. The excess of borane was destroyed with ethanol (3 mL). The mixture was cooled at 0° C. 30% hydrogen peroxyde (1 mL) and 3N aqueous solution of sodium hydroxyde (1 mL) were added. The mixture was refluxed during 2 h. The reaction mixture was diluted with water and extracted three times with ethyl acetate. The organic layer was dried over sodium sulfate, filtered and concentrated under reduced pressure to afford an oil. Flash chromatography on silica gel and elution with a 1:1 mixture of ethyl acetate and hexane afforded the expected alcohol 1,2,3,4-di-O-isopropylidene-1-(2-hydroxyethyl) -β-D-arabinopyranose (1.717 g, 80%) as an oil.

EXAMPLE 47

Preparation of 1,2,3,4-Di-O-Isopropylidene-1-(2-Iodoethyl)-β-D-Arabinopyranose

To a solution of 1,2,3,4-di-O-isopropylidene-1-(2-hydroxyethyl)-β-D-arabinose (1.7 g, 6.2 mmol) in dry methylene chloride (30 mL) was added triethylamine (1.3 mL, 9.3 mmol). Then the mixture was cooled to −10° C. and mesylchloride (0.5 mL, 6.46 mmol) was added dropwise. The mixture was stirred an additional 15 min at −10° C., then the reaction was allowed to warm up to room temperature. The mixture was washed three times with water. The organic phase was dried over sodium sulfate, filtered and concentrated under reduced pressure to afford a yellow oil which was used without purification. The crude 1,2:3,4-di-O-isopropylidene-1-(2-methylsulfonyloxyethyl)-α-D-arabinose was dissolved in ether (15 mL). To this mixture a 0.35M solution of magnesium iodide in ether (53 mL) was added at 0° C. The mixture was stirred 15 min at 0° C. The excess of magnesium iodide was hydrolized with water. The reaction mixture was washed with aqueous sodium thiosulfate and water. The organic layer was dried over sodium sulfate, filtered and concentrated under reduced pressure to afford an oil. Flash chromatography on silica gel and elution with a 9:1 mixture of hexane and ethylacetate afforded the expected iodide 1,2,3,4-di-O-isopropylidene-1-(2-iodoethyl) -β-D-arabinopyranose (1.9 g, 80%) as a slightly yellow oil.

EXAMPLE 48

Preparation of 2,3,5-Tri-O-Benzyl-1,4-Dideoxy-1,4-{[2-(1,2:3,3-Di-O-Isopropylidene -1-β-D-Arabinopyranosyl)Ethyl]Imino}-D-Arabinitol A solution of 1,2,3,4-di-O-isopropylidene-1-(2-iodoethyl)-β-D-arabinose (2.0 g, 5.21 mmol) and 2,3,5-tri-O-benzyl-1,4-dideoxy-1,4-imino-D-arabinitol (0.7 g, 1.74 mmol) in dry dimethylformamide (10 mL) was heated at 80° C. overnight along with dry potassium carbonate (0.91 g, 6.6 mmol). The dimethylformamide was evaporated under reduced pressure. The residue was taken with ethyl acetate and washed twice with water. The organic layer was dried over sodium sulfate, filtered and concentrated under reduced pressure to afford an oil. Chromatography on neutral aluminum oxyde activity III and elution with a graded mixture of hexane and ethyl acetate afforded the expected amine 2,3,5-tri-O-benzyl-1,4-dideoxy-1,4{[2-(1,2,3,4-di-O-isopropylidene -1-β-D-arabinopyranosyl)]imino}-D-arabinitol (0.88 g, 61%) as a foam.

EXAMPLE 49

Preparation of 2,3,5-Tri-O-Benzyl-1,4-Dideoxy-1,4-{[2-(1-O-Methyl-1-α-D-Arabinofuranosyl) Ethyl]Imino}-D-Arabinitol 2,3,5-tri-O-benzyl-1,4-dideoxy-1,4-{[2-(1,2,3,4-di-O-isopropylidene-1-β-D-arabinopyranosyl) ethyl]imino}-D-arabinitol (0.70 g, 0.94 mmol) was dissolved in methanol (60 mL) containing 5% of dry hydrochloric acid and was refluxed during 24 h. The reaction mixture was cooled to room temperature and neutralized with Amberlyst A26 OH⊖ form. The mixture was filtered and the solvent was evaporated under reduced pressure to give a foam. Flash chromatography on silica gel and elution with a graded mixture of ethylacetate and methanol afforded the expected amine 2,3,5-tri-O-benzyl-1,4-dideoxy-1,4-{[2-(1-O-methyl-1-α-d-arabinofuranosyl)ethyl]-imino}-D-arabinitol (0.36 g, 65%) as a foam.

EXAMPLE 50

Preparation of 1,4-Dideoxy-1,4-{[2-(1-O-Methyl-1-α-D-Arabinofuranosyl)Ethyl]Imino}-D-Arabinitol The amine 2,3,5-tri-O-benzyl-1,4-dideoxy-1,4-{[2-(1-O-methyl-1-α-D-arabinofuranosyl) ethyl]imino}-D-arabinitol (0.3 g, 0.51 mmol) was dissolved in acetic acid (20 mL). Palladium 10% on charcoal (0.2 g) was added and the mixture was hydrogenated during 4 days at 3 atmosphere. The catalyst was removed by filtration and the solvents were evaporated under reduced pressure. The residue was dissolved in water and passed through a column of Amberlyst A26 OH⊖ form. Water was evaporated under reduced pressure. Flash chromatography on silica gel and elution with a graded mixture of chloroform, methanol and water afforded the expected amine 1,4-dideoxy-1,4-{[2-(1-O-methyl-1-α-D-arabinofuranosyl) ethyl]-imino}-D-arabinitol (0.115 g, 70%) as an amorphous solid.

EXAMPLE 51

Preparation of Methyl 6-O-(4-O-Acetyl-2,3,6-Tri-O-Benzyl-α-D-Galactopyranosyl)-2,3,4-Tri-O-Benzyl-α-D-Glucopyranoside Ethereal silver perchlorate (0.08M, 76.9 mL, 6.15 mmol) was added with stirring at −30° C. to a solution of methyl 2,3,4-tri-O-benzyl-α-D-glucopyranoside (2.078 g, 4.48 mmol), 4-O-acetyl-2,3,6-tri-O-benzyl-α-D-galactopyranosyl chloride (2.859 g, 5.6 mmol) and 2,4,6-trimethylpyridine (0.81 mL, 6.15 mmol) in ether (20 mL). The mixture was stirred 15 min at −30° C. and silver chloride precipitated. The mixture was filtered through a celite pad, the solids were washed with ether, the filtrate was concentrated under reduced pressure. The residue was dissolved in methylene chloride and the organic layer was washed successively with aqueous sodium thiosulfate and water. The organic layer was dried over sodium sulfate, filtered and concentrated under reduced pressure to afford a foam. Flash chromatography on silica gel and elution with a graded mixture of hexane and ethyl acetate afforded methyl 6-O-(4-O-acetyl-2,3,6-tri-O-benzyl-α-D-galactopyranosyl) -2,3,4-tri-O-benzyl-α-D-glucopyranoside (2.314 g, 55%) as a foam.

EXAMPLE 52

Preparation of Methyl 2,3,4-Tri-O-Benzyl-6-O-(2,3,6-Tri-O-Benzyl-α-D-Galactopyranosyl) -α-D-Glucopyranoside Methyl 6-O-(4-O-acetyl-2,3,6-tri-O-benzyl-α-D-galactopyranosyl)-2,3,4-tri-O-benzyl -α-D-glucopyranoside (2.314 g, 2.46 mmol) was dissolved in hot toluene (20 mL) and methanol (80 mL) was added, followed by a few drops of 1M. methanolic sodium methoxide. The mixture was stirred at room temperature during 2 h. The reaction mixture was made neutral with Amberlite IR 120 (H+) resin, filtered and concentrated under reduced pressure to afford methyl 2,3,4-tri-O-benzyl-6-O-(2,3,6-tri-O-benzyl-α-D-galactopyranosyl) -α-D-glucopyranoside (2.21 g, 100%) as an amorphous solid.

EXAMPLE 53

Preparation of Methyl 6-O-(2,3,6-Tri-O-Benzyl-4-O-Trifluoromethylsulfonyl-α-D-Galactopyranosyl) -2,3,4-Tri-O-Benzyl-α-D-Glucopyranoside To a solution of dry pyridine (0.45 mL) in dry methylene chloride (40 mL) cooled to −15° C. was added trifluoromethanesulfonic anhydride (0.83 mL). The mixture was stirred during 15 min at −10° C., then methyl 2,3,4-tri-O-benzyl-6-O-(2,3,6-tri-O-benzyl -α-D-galactopyranosyl)-α-D-glucopyranoside (2.21 g, 2.46 mmol) in methylene chloride (10 mL) was added. The mixture was washed with water. The organic layer was dried over sodium sulfate, filtered and concentrated under reduced pressure to afford an oil (2.478 g, 98%) which was the expected triflate methyl 6-O-(2,3,6-tri-O-benzyl-4-O-trifluoromethylsulfonyl-α-D-galactopyranosyl) -2,3,4-tri-O-benzyl-α-D-glucopyranoside.

EXAMPLE 54

Preparation of 2,3,5-Tri-O-Benzyl-1,4-dideoxy-N-[2,3,6-Tri-O-Benzyl-Deoxy-1-(2,3,4-Tri -O-Benzyl-1-O-Methyl-6-O-α-D-glucopyranosyl)-α-D-Glucopyranosyl]-1,4-Imino-D-Arabinitol A solution of methyl 6-O-(2,3,6-tri-O-benzyl-4-O-trifluoromethysulfonyl-α-D-galactopyranosyl) -2,3,4-tri-O-benzyl-α-D-glucopyranoside (1.2 g, 1.16 mmol) and 2,3,5-tri-O-benzyl-1,4-dideoxy-1,4-imino-D-arabinitol (0.468 g, 1.16 mmol) in ethanol-free chloroform (50 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford a foam. Flash chromatography on silica gel and elution with a graded mixture of hexane and ethyl acetate afforded the expected amine 2,3,5-tri-O-benzyl-1,4-dideoxy-N-[2,3,6-tri-O-benzyl-4-deoxy -1-(2,3,4-tri-O-benzyl-1-O-methyl-6-O-α-D-gluco-pyranosyl)-α-D-glucopyranosyl]-1,4-imino-D-arabinitol (0.668 g, 45%) as an amorphous solid.

EXAMPLE 55

Preparation of 1,4-Dideoxy-N-[4-Deoxy-1-(1-O-Methyl-6-O-α-D-Glucopyranosyl) -α-D-Glucopyranosyl]-1,4-Imino-D-Arabinitol 2,3,5-tri-O-benzyl-1,4-dideoxy-N-[2,3,6-tri-O-benzyl-4-deoxy-1-(2,3,4-tri -O-benzyl-1-O-methyl-6-O-α-D-glucopyranosyl)-α-D-glucopyranosyl]-1,4-imino-D-arabinitol (0.6 g, 0.468 mmol) was dissolved in acetic acid (30 mL). Palladium 10% on charcoal (0.6 g) was added. The mixture was hydrogenated during 4 days at 3 atmospheres. The catalyst was removed by filtration and the solvents were evaporated under reduced pressure. The residue was dissolved in water and passed through a column of Amberlyst A26 OH⊖ form. Water was evaporated under reduced pressure and flash chromatography on silica gel and elution with a graded mixture of chloroform, methanol and water afforded the expected amine 1,4-dideoxy-N-[4-deoxy-1-(1-O-methyl-6-O-α-D-glucopyranosyl) -α-D- glucopyranosyl]-1,4-imino-D-arabinitol (0.154 g, 70%) as an amorphous solid.

EXAMPLE 56

Preparation of 2,3,6-Tri-O-Benzyl-4-Deoxy-4-Hydroxymethyl-D-Glucopyranose

Methyl 2,3,6-tri-O-benzyl-4-deoxy-4-hyroxymethyl-α-D-glucopyranoside (4.78 g, 10 mmol) was dissolved at 0° C. in a 9:1 mixture of trifluoracetic acid and water (50 mL). The mixture was stirred overnight at 0° C. The solvents were evaporated under reduced pressure without heating. The residue was dissolved in ethyl acetate and washed successively with sodium bicarbonate and brine. The organic layer was dried over sodium sulfate, filtered and concentrated under reduced pressure to afford an oil. Flash chromatography on silica gel and elution with a graded mixture of ethyl acetate and hexane afforded 2,3,6-tri-O-benzyl-4-deoxy-4-hydroxymethyl-D-glucopyranose (4.4 g, 95%) as an oil.

EXAMPLE 57

Preparation of Acetyl 2,3,6-Tri-O-Benzyl-4-Deoxy-4-Acetyloxymethyl-D-Glucopyranoside 2,3,6-tri-O-benzyl-4-deoxy-4-hydroxymethyl-D-glucopyranose (5.10, 9.30 mmol) was dissolved in dry pyridine (25 mL) and acetic anhydride (5 mL) was added. The mixture was stirred during 24 h at room temperature. The solvent was evaporated under high vacuum. The residue was dissolved in ethyl acetate and washed with water. The organic layer was dried over sodium sulfate, filtered and concentrated under reduced pressure to afford the expected diacetate acetyl 2,3,6-tri-O-benzyl-4-deoxy-4-acetyloxymethyl -D-glucopyranoside (5.10 g, 98%) as an oil which was used without purification.

EXAMPLE 58

Preparation of 2,3,6-Tri-O-Benzyl-1,4-Dideoxy-4-Acetyloxymethyl-D-Glucopyranosyl Chloride Acetyl 2,3,6-tri-O-benzyl-4-deoxy-4-acetyloxymethyl-D-glucopyranoside (5.10 g, 9.30 mmol) in ether (10 mL) was treated with ethereal hydrogen chloride (0.2 g/mL, 25 mL). The mixture was stirred at room temperature during 48 h. The solvents were evaporated under reduced pressure to afford an oil. Flash chromatography on silica gel and elution with a graded mixture of carbon tetrachloride and ethyl acetate afforded 2,3,6-tri-O-benzyl-1,4-dideoxy-4-acetyloxymethyl-D-glucopyranosyl chloride (3.661 g, 75%) as an oil.

EXAMPLE 59

Preparation of Methyl 4-O-(2,3,6-Tri-O-Benzyl-4-Deoxy-4-Acetyloxymethyl-α-D-Glucopyranosyl) -2,3,6-Tri-O-Benzyl-α-D-Glucopyranoside Ethereal silver perchloride (0.08M, 9.58 mL, 7.67 mmol) was added with stirring at −30° C. to a solution of methyl 2,3,6-tri-O-benzyl-α-D-glucopyranoside (2.592 g, 5.59 mmol), 2,3,6-tri-O-benzyl-1,4-dideoxy-4-acetyloxymethyl-D-gluco-pyranosyl chloride (3.661 g, 6.98 mmol) in ether (20 mL). The mixture was stirred 15 min at −30° C. and silver chloride precipitated. The mixture was filtered through a celite pad, the solids were washed with ether, the filtrate was concentrated under reduced pressure. The residue was dissolved in methylene chloride and the organic layer was washed successively with aqueous sodium thiosulfate and water. The organic layer was dried over sodium sulfate, filtered and concentrated under reduced pressure to afford a foam. Flash chromatography on silica gel and elution with a graded mixture of hexane and ethyl acetate afforded mehyl 4-O-(2,3,6-tri-O-benzyl-4-deoxy-4-acetyloxymethyl-α-D-glucopyranosyl) -2,3,6-tri-O-benzyl-α-D-glucopyranoside (3.19 g, 60%) as a foam.

EXAMPLE 60

Preparation of Methyl 4-O-(2,3,6-Tri-O-Benzyl-4-Deoxy-4-Hydroxymethyl-α-D-Glucopyranosyl) -2,3,6-Tri-O-Benzyl-α-D-Glucopyranoside Methyl 4-O-(2,3,6-tri-O-benzyl-4-deoxy-4-acetyloxymethy-α-D-glucopyranosyl) -2,3,6-tri-O-benzyl-α-D-glucopyranoside (3.19 g, 3.35 mmol) was dissolved in hot toluene (20 mL) and methanol (80 mL) was added, followed by a few drops of 1M. methanolic sodium methoxide. The mixture was stirred at room temperature during 2 h. The reaction mixture was made neutral with Amberlite IR 120 ($H^{30}$) resin, filtered and concentrated under reduced pressure to afford methyl 4-O-(2,3,6-tri-O-benzyl-4-deoxy-4-hydroxymethyl -α-D-glucopyranosyl)-2,3,6-tri-O-benzyl-α-D-glucopyranoside (3.049 g, 100%) as an amorphous solid.

EXAMPLE 61

Preparation of Methyl 4-O-(2,3,6-Tri-O-Benzyl-4-Deoxy-4-Trifluoromethylsulfonyloxmethyl -α-D-Glucopyranosyl)-2,3,6-Tri-O-Benzyl-α-D-Glucopyranoside To a solution of dry pyridine (0.6 mL) in dry methylene chloride (50 mL) cooled to −15° C. was added trifluoromethanesulfonic anhydride (1.12 mL). The mixture was stirred during 15 min at −10° C., then methyl 4-O-(2,3,6-tri-O-benzyl-4-deoxy-4-hydroxymethyl -α-D-glucopyranosyl)-2,3,6-tri-O-benzyl-α-D-glucopyranoside (3.049 g, 3.35 mmol) in methylene chloride (15 mL) was added. The mixture was washed with water. The organic layer was dried over sodium sulfate, filtered and concentrated under reduced pressure to afford an oil (3.42 g, 98%) which was the expected triflate methyl 4-O-(2,3,6-tri-O-benzyl-4-deoxy-4-trifluoromethylsulfonyloxymethyl -α-D-glucopyranosyl)-2,3,6-tri-O-benzyl-α-D-glucopyranoside.

EXAMPLE 62

Preparation of 2,3,5-Tri-O-Benzyl-1,4-Dideoxy-N-{[2,3,6-Tri-O-Benzyl-4-Deoxy-1-(2,3,6-Tri -O-Benzyl-4-O-α-D-Glucopyranosyl)-4-α-D-Glucopyranosyl]Methyl}4-Imino-D-Arabinitol A solution of methyl 4-O-(2,3,6-tri-O-benzyl-4-deoxy-4-trifluoromethylsulfonyloxymethyl-α-D-glucopyranosyl) -2,3,6-tri-O-benzyl-α-D-glucopyrano-side (1.56 g, 1.50 mmol) and 2,3,5-tri-O-benzyl-1,4-dideoxy -1,4-imino-D-arabinitol (0.605 g, 1.50 mmol) in ethanol-free chloroform (50 mL) was refluxed under nitrogen during 48 h. The mixture was diluted in methylene chloride and washed successively with a saturated brine. The organic layer was dried over sodium sulfate, filtered and concentrated under reduced pressure to afford a foam. Flash chromatography on silica gel and elution with a graded mixture of hexane and ethyl acetate afforded the expected amine 2,3,5-tri-O-benzyl-1,4-dideoxy-N-{[2,3,6-tri-O-benzyl -4-deoxy-1-(2,3,6-tri-O-benzyl-1-O-methyl-4-O-α-D-glucopyranosyl) -4-α-D-glucopyranosyl]methyl}1,4-imino-D-arabinitol (0.922 g, 48%) as an amorphous solid.

EXAMPLE 63

Preparation of
1,4-Dideoxy-N-{[4-Deoxy-1-(1-O-Methyl-4-O-α-D-Glucopyranosyl)-4-α-D-Glucopyranosyl]Methyl}1,4-Imino-D-Arabinitol 2,3,5-tri-O-benzyl-1,4-dideoxy-N-{[2,3,6-tri-O-benzyl-4-deoxy-1-(2,3,6-tri -O-benzyl-1-O-methyl-4-O-α-D-glucopyranosyl)-4α-D-glucopyranosyl]methyl}1,4-imino-D-arabinitol (0.90 g, 0.702 mmol) was dissolved in acetic acid (40 mL). Palladium 10% on charcoal (0.6 g) was added. The mixture was hydrogenated during 4 days at 3 atmosphere. The catalyst was removed by filtration and the solvents were evaporated under reduced pressure. The residue was dissolved in water and passed through a column of Amberlyst A26 OH⊖. Water was evaporated under reduced pressure and flash chromatography on silica gel and elution with a graded mixture of chloroform, methanol and water afforded the expected amine 1,4-dideoxy-N-{[4-deoxy-1-(1-O-methyl-4-O-α-D-glucopyranosyl)-4-α-D-glucopyranosyl]methyl}1,4-imino-D-arabinitol (0.244 g, 74%) as an amorphous solid.

EXAMPLE 64

Preparation of Methyl
6-O-(2,3,6-Tri-O-Benzyl-4-Deoxy-4-Acetyloxymethyl-α-D-Glucopyranosyl)
-2,3,4-Tri-O-Benzyl-α-D-Glucopyranoside Ethereal silver perchlorate (0.08M, 76.7 mL, 6.13 mmol) was added with stirring at −30° C. to a solution of methyl 2,3,4-tri-O-benzyl-α-D-glucopyranoside (2.074 g, 4.472 mmol), 2,3,6-tri-O-benzyl-1,4-dideoxy-4-acetyloxymethyl-D-gluco-pyranosyl chloride (6.13 mmol) and 2,4,6-trimethylpyridine (0.80 mL, 6.13 mmol) in ether (20 mL). The mixture was stirred 15 min at −30° C. and silver chloride precipitated. The mixture was filtered through a celite pad, the solids were washed with ether, the filtrate was concentrated under reduced pressure. The residue was dissolved in methylene chloride and the organic layer was washed successively with aqueous sodium thiosulfate and water. The organic layer was dried over sodium sulfate, filtered and concentrated under reduced pressure to afford a foam. Flash chromatography on silica gel and elution with a graded mixture of hexane and ethyl acetate afforded methyl 6-O-(2,3,6-tri-O-benzyl-4-deoxy-4-acetyloxymethyl -α-D-glucopyranosyl)-2,3,4-tri-O-benzyl-α-D-glucopyranoside (2.469 g, 58%) as a foam.

EXAMPLE 65

Preparation of Methyl
6-O-(2,3,6-Tri-O-Benzyl-4-Deoxy-4-Hydroxymethyl-α-Glucopyranosyl)
-2,3,4-Tri-O-Benzyl-α-D-Glucopyranoside Methyl 6-O-(2,3,6-tri-O-benzyl-4-deoxy-4-acetyloxymethyl-α-D-glucopyranosyl) -2,3,4-tri-O-benzyl-α-D-glucopyranoside (2.469 g, 2.593 mmol) was dissolved in hot toluene (20 mL) and methanol (80 mL) was added, followed by a few drops of 1M. methanolic sodium methoxide. The mixture was stirred at room temperature during 2 h. The reaction mixture was made neutral with Amberlite IR 120 (H+) resin, filtered and concentrated under reduced pressure to afford methyl 6-O-(2,3,6-tri-O-benzyl-4-deoxy-4-hydroxymethyl -α-D-glucopyranosyl)-2,3,4-tri-O-benzyl-α-D-glucopyranoside (2.36 g, 100%) as an amorphous solid.

EXAMPLE 66

Preparation of Methyl
6-O-(2,3,6-Tri-O-Benzyl-4-Deoxy-4-Trifluoromethylsulfonyloxymethyl
-α-D-Glucopyranosyl)-2,3,4-Tri-O-Benzyl-α-D-Glucopyranoside To a solution of dry pyridine (0.46 mL) in dry methylene chloride (40 mL) cooled to −15° C. was added trifluoromethanesulfonic anhydride (0.86 mL). The mixture was stirred during 15 min at −10° C., then methyl 6-O-(2,3,6-tri-O-benzyl-4-deoxy-4-hydroxymethyl -α-D-glucopyranosyl)2,3,4-tri-O-benzyl-α-D-glucopyranoside (2.36 g, 2.593 mmol) in methylene chloride (10 mL) was added. The mixture was stirred during 1.5 h at −10° C. The reaction mixture was washed with water. The organic layer was dried over sodium sulfate, filtered and concentrated under reduced pressure to afford an oil (2.65 g, 98%) which was the expected triflate methyl 6-O-(2,3,6-tri-O-benzyl-4-deoxy-4-trifluoromethylsulfonyloxymethyl -α-D-glucopyranosyl)-2,3,4-tri-O-benzyl-α-D-glucopyranoside.

EXAMPLE 67

Preparation of
2,3,5-Tri-O-Benzyl-1,4-Dideoxy-N-{[2,3,6-Tri-O-Benzyl-4-Deoxy-1-(2,3,4-Tri-O-Benzyl-1-O-Methyl-6-O-α-D-Glucopyranosyl)-4-α-D-Glucopyranosyl]Methyl}1,4-Imino-D-Arabinitol A solution of methyl 6-O-(2,3,6-tri-O-benzyl-4-deoxy-4-trifluoromethylsulfonyloxymethyl-α-D -glucopyranosyl)-2,3,4-tri-O-benzyl-α-D-glucopyranoside (1.465 g, 1.40 mmol) and 2,3,5-tri-O-benzyl -1,4-dideoxy-1,4-imino-D-arabinitol (0.564 g, 1.40 mmol) in ethanol-free chloroform (50 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford a foam. Flash chromatography on silica gel and elution with a graded mixture of hexane and ethyl acetate afforded the expected amine 2,3,5-tri-O-benzyl-1,4-dideoxy-N-{[2,3,6-tri -O-benzyl-4-deoxy-1-(2,3,4-tri-O-benzyl-1-O-methyl-6-O-α-D-glucopyranosyl) -4-α-D-glucopyranosyl]methyl}1,4-imino-D-arabinitol (1.2 g, 67%) as an amorphous solid.

EXAMPLE 68

Preparation of
1,4-Dideoxy-N-{[4-Deoxy-1-(1-O-Methyl-6-O-α-D-Glucopyranosyl)-4-α-D-Glucopyranosyl]Methyl}1,4-Imino-D-Arabinitol 2,3,5-tri-O-benzyl-1,4-dideoxy-N-{[2,3,6-tri-O-benzyl-4-deoxy-1-(2,3,4-tri-O-benzyl -1-O-methyl-6-O-α-D-glucopyranosol)-4-α-D-glucopyranosyl]methyl}1,4-imino-D-arabinitol (1.1 g, 0.859 mmol) was dissolved in acetic acid (30 mL). Palladium 10% on charcoal (0.6 g) was added. The mixture was hydrogenated during 4 days at 3 atmosphere. The catalyst was removed by filtration and the solvents were evaporated under reduced pressure. The residue was dissolved in water and passed through a column of Amberlyst A26 OH⊖. Water was evaporated under reduced pressure and flash chromatography on silica gel and elution with a graded mixture of chloroform, methanol and water afforded the expected amine 1,4-dideoxy-N-{[4-deoxy-1-(1-O-methyl-6-O-α-D -glucopyranosyl)-4-α-D-glucopyranosyl]methyl}1,4-imino-D-arabinitol (0.303 g, 75%) as an amorphous solid.

EXAMPLE 69

Preparation of 1,5-Dideoxy-1,5-(6-Deoxy-6-D-Glucopyranosyl)Imino-D-Arabinitol 1,4-dideoxy-1,4-(6-deoxy-1-O-methyl-6-α-d-glucopyranosyl)imino-D-arabinitol (0.2 g, 0.647 mmol) was dissolved in a 1:1 mixture of water and trifluoroacetic acid (10 mL). The mixture was stirred during 24 h at 0° C. The solvents were evaporated under reduced pressure to afford a foam. Chromatography on Amberlyst A26 OH⊖ form afforded the expected amine 1,5-dideoxy-1,5-(6-deoxy-6-D-glucopyranosyl) imino-D-arabinitol (0.181 g, 95%).

EXAMPLE 70

Preparation of Methyl 2,3,4-Tri-O-Benzyl-6-O-Trifluoromethylsulfonyl-β-D-Glucopyranoside To a solution of dry pyridine (0.456 mL) in methylene chloride (20 mL) cooled to −15° C. was added trifluoromethanesulfonic anhydride (0.864 mL). The mixture was stirred during 15 min at −10° C., then methyl 2,3,4-tri-O-benzyl-β-D-glucopyranoside (1.2 g, 2.58 mmol) in methylene chloride (30 mL) was added [P. Kovac, J. Alföldi and M. Kósik, Chem. Zvesti 28, 820, (1974)]. The mixture was stirred during 1.5 h at −10° C. The reaction mixture was washed with water. The organic layer was dried over sodium sulfate, filtered and concentrated under reduced pressure to afford an oil. Flash chromatography on silica gel and elution with a 7:2 mixture of hexane and ethyl acetate afforded the expected compound methyl 2,3,4-tri-O-benzyl-6-O-trifluoromethylsulfonyl -β-D-glucopyranoside (1.408 g, 89%) as an oil, which crystallized in the fridge.

EXAMPLE 71

Preparation of 2,3,5-Tri-O-Benzyl-1,4-[(2,3,4-Tri-O-Benzyl-6-Deoxy-1-O-Methyl -6-β-D-Glucopyranosyl)Imino]-D-Arabinitol A solution of methyl 2,3,4-tri-O-benzyl-6-O-trifluoromethylsulfonyl-β-D-glucopyranoside (0.7 g, 1.17 mmol) and 2,3,5-tri-O-benzyl-1,4-dideoxy-1,4-imino-D-arabinitol (0.395 g, 1 mmol) in ethanol-free chloroform (20 mL) was refluxed under nitrogen during 48 h. The mixture was diluted in methylene chloride and washed successively with a saturated aqueous solution of sodium bicarbonate and saturated brine. The organic layer was dried over sodium sulfate, filtered and concentrated under reduced pressure to afford an oil. Flash chromatography on silica gel and elution with a 9:10 mixture of toluene and ethyl acetate afforded the expected compound 2,3,5-tri-O-benzyl-1,4-dideoxy-1,4-[(2,3,4-tri -O-benzyl-6-deoxy-1-O-methyl-6β-D-glucopyranosyl-)imino]-D-arabinitol, as a white foam (0.398 g. 40%).

EXAMPLE 72

Preparation of 1,4-Dideoxy-1,4-[(6-Deoxy-1-O-Methyl-6-β-D-Glucopyranosyl)Imino]-D-Arabinitol 2,3,5-tri-O-benzyl-1,4-dideoxy-1,4-[(2,3,4-tri-O-benzyl-6-deoxy-1-O-methyl-6-β-D-glucopyranosyl)imino]-D-arabinitol (0.398 g, 0.469 mmol) was dissolved in a 1:1 mixture of methanol and acetic acid (40 mL) and Pd 10% on charcoal (70 mg) was added. The mixture was stirred under hydrogen at 3 bars during 3 days. The catalyst was filtered off and the solvents were evaporated under reduced pressure. The residue was dissolved in water and passed through a column of Amberlyst A26 OH⊖ form. Evaporation of water under reduced pressure afforded an amorphous solid. Flash chromatography on silica gel and elution with a 50:50:4 mixture of chloroform, methanol and water afforded 1,4-dideoxy-1,4-[(6-deoxy-1-O-methyl-6-β-D-glucopyranosyl)imino]-D-arabinitol as an amorphous solid (0.39 g, 27%).

Enzymes which catalyze the hydrolysis of complex carbohydrates. e.g. α-glycosidases, convert non-absorbable carbohydrates into absorbable sugars. The rapid action of these enzymes, particularly following the intake of high levels of carbohydrates, leads to acute high levels in blood glucose which, in the case diabetics, lead to undesirable manifestations. Thus it has been a long-sought goal to find compounds which will obviate the hyperglicemia caused by dietary improprieties. Similarly, in the case of obesity the control of high levels of blood glucose, with its subsequent conversion to fat, caused by the catalysis of carbohydrates has inspired the quest for compounds which will obviate the problems associated with dietary improprieties.

The compounds of this invention (I) are potent and lasting inhibitors of α-glucosidase as established by using standard laboratory methods. In these methods, serum glucose levels are determined. As a result of their activity as α-glucosidase inhibitors, the compounds can be used for the treatment of disease states caused by the underutilization and/or overproduction of serum glucose without adversely affecting the rate of transport across cell membranes. Thus, the compounds are useful in the treatment of diabetes and obesity.

In the practice of this invention, an effective amount of a compound of this invention is that amount required to reduce the amount of serum glucose (relative to a control) following the ingestion of carbohydrates convertible to absorbable glucose. The specific dosage for the treatment of any specific patient suffering from either disease state will depend upon such factors as size, type and age of the patient as well as the severity of the disease state, all of which are factors normally familiar to and considered by the attending diagnostician treating the patient. Generally, the compounds are to be administered orally at a dose of 0.2 to 20 milligrams per kilogram of body weight (MPK) with a dose of 0.5 to 5 MPK being preferred. The compounds preferably are to be administered orally at mealtimes in single or multiple unit doses containing 25 mg to 250 mg. Of course, in the treatment of obesity, the term includes not only the treatment of the disease, but also includes the prevention of obesity by continued administration of dose regimens suitable for the maintenance of the desired weight for the patient.

It is also to be found that the compounds of the instant invention (I) will exert an inhibitory effect on glycosidase enzymes that are essential for elaboration of the final structure of the oligosaccharide side-chains of glyco-proteins, particularly the HIV (gp 120) glycoprotein. Suitable assay techniques, e.g., syncytial formation, the reverse transcriptase assay, immunofluorescence tests and election microscopy may be used to evaluate the effects on HIV viral growth and for determining dose regimens. Antiviral effects may be confirmed by immunofluorescence with serum for virally infected patients. In the treatment of the HIV related disease states, as well as other retroviral glyco-protein-related disease states, unlike the treatment of diabetes and obesity, the compounds of this invention may be administered by parenteral means; specific doses being within the above stated dose range for treatment of diabetes and obesity.

In practising the end-use application of the compounds of this invention, the compounds are preferably incorporated in a pharmaceutical formulation comprising a pharmaceutical carrier in admixture with a compound of this invention. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

We claim:

1. 1,4-Dideoxy-1,4-imino-d-arabinitol derivatives of the formula

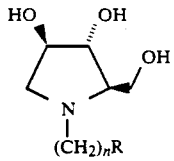

the optical and geometric isomers and the pharmaceutically acceptable acid addition salts thereof, wherein n is zero, one or two, and R is a glycosyl or etherified or acylated glycosyl radical containing from 1 to 3 hexose or pentose units, said etherified or acylated glycosyl radical bearing the ether or acyl radical at the hydroxyl moiety located on the anomeric carbon atom.

2. A compound of claim 1 wherein R is a glucosyl, galactosyl, fucosyl, fructosyl, mannosyl, ribosyl, arabinosyl, xylosyl, allosyl, altrosyl, gulosyl, idosyl, talosyl, lyxosyl, isomaltosyl, trehalosyl α and β cellobiosyl, maltosyl, maltotriosyl or cellotriosyl radical.

3. A compound of claim 1 wherein R is 6-glucosyl, 4-glucosyl, 1-fructosyl, 6-fructosyl, 6-maltosyl, 4-maltosyl, 6-isomaltosyl or 4-isomaltosyl.

4. A compound of claim 1, said compound being 1,4-dideoxy-1,4-[(6-deoxy-1-O-methyl-6-α-D-glucopyranosyl)imino]-D-arabinitol.

5. A compound of claim 1, said compound being 1,4-dideoxy-1,4-[(6,7-dideoxy-1-O-methyl-7-α-D-glucoheptopyranosyl)imino]-D-arabinitol.

6. A compound of claim 1, said compound being 1,4-dideoxy-1,4-[(1-deoxy-2-O-methyl-α-D-fructofuranosyl) imino]-D-arabinitol.

7. A compound of claim 1, said compound being 1,4-dideoxy-1,4-[(4-deoxy-1-O-methyl-4-α-D-glucopyranosyl) imino]-D-arabinitol.

8. A compound of claim 1, said compound being 1,4-dideoxy-N-[6-deoxy-1-(1-O-methyl-6-O-α-D-glucopyranosyl]-1,4-imino-D-arabinitol.

9. A compound of claim 1, said compound being 1,4-dideoxy-N-[6,7-dideoxy-1(1-O-methyl-6-O-α-D-glucopyranosyl)-α-D-glucoheptopyranosyl]-1,4-imino-D-arabinitol.

10. A compound of claim 1, said compound being 1,4-dideoxy1,4-[(4-deoxy-1-O-methyl-4-α-D-glucopyranosyl)methylimino]-D-arabinitol.

11. A compound of claim 1, said compound being 1,4-dideoxy-N-[4-deoxy-1-(1-O-methyl-4-O-α-D-glucopyranosyl)-α-D-glucopyranosyl]-1,4-imino-D-arabinitol.

12. A compound of claim 1, said compound being 1,4-dideoxy-1,4-{[2-(1-O-methyl-1-α-D-arabinofuranosyl)ethyl]imino}-D-arabinitol.

13. A compound of claim 1, said compound being 1,4-dideoxy-N-[4-deoxy-1-(1-O-methyl-6-O-α-D-glucopyranosyl]-1,4-imino-D-arabinitol.

14. A compound of claim 1, said compound being 1,4-dideoxy-N-([4-deoxy-1-(1-O-methyl-4-O-α-D-glucopyranosyl]methyl}-1,4-imino-D-arabinitol.

15. A compound of claim 1, said compound being 1,4-dideoxy-N-{[4-deoxy-1-(1-O-methyl-6-O-α-D-glucopyranosyl)-4-α-D-glucopyranosyl]methyl}-1,4-imino-D-arabinitol.

16. A compound of claim 1, said compound being 1,4-dideoxy-1,4-(6-deoxy-6-D-glucopyranosyl) imino-D-arabinitol.

17. A compound of claim 1, said compound being 1,4-dideoxy-1,4-(6-deoxy-1-O-D-methyl-6-β-O-glucopyranosyl)imino-D-arabinitol.

18. A method for inhibiting α-glucosidase enzymes which comprises administering thereto an effective amount of a compound of claim 1.

19. A method for treating diabetes which comprises administering to a patient suffering from a diabetes a therapeutically effective amount of a compound of claim 1.

20. A method for controlling obesity which comprises administering to a patient an amount of a compound of claim 1 sufficient to reduce the amount of systematically absorbable glucose following ingestion of food substances capable of being enzymatically converted to glucose.

21. A process for preparing a compound of the formula

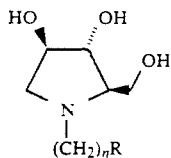

the optical and geometric isomers and the pharmaceutically acceptable salts thereof, wherein n is zero, one or two, R is a glycosyl or etherified or acylated glycosyl radical containing from 1 to 3 hexose or pentose units, said etherified or acylated glycosyl radical bearing the ether or acyl radical at the hydroxyl moiety located on the anomeric carbon atom which comprises condensing a compound of the formula

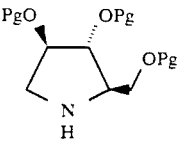

with a compound of the formula

R'(CH$_2$)$_n$X wherein X is a halide or triflate, n is zero, one or two, R' is a hydroxy-protected glycosyl or etherified or acetylated glycosyl radical containing from 1 to 3 hexose or pentose units, said etherified or acylated glycosyl radical bearing the ether or acyl radical at the hydroxyl moiety located on the anomeric carbon atom to produce a compound of the formula

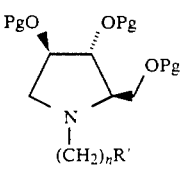

which compound is deprotected, followed by an optional conversion to a pharmaceutically acceptable salt thereof.

* * * * *

UNITED STATES PATENT AND TRADEMARK OFFICE
CERTIFICATE OF CORRECTION

PATENT NO. : 5,097,023

DATED : March 17, 1992

INVENTOR(S) : Jean-Bernard Ducep and Charles Danzin

It is certified that error appears in the above-identified patent and that said Letters Patent is hereby corrected as shown below:

At column 1, line 33, "carbon atoms" should read --carbon atom--.

At column 1, line 34, "salts forms" should read --salt forms--.

At column 3, line 64, "group shave" should read --groups have--.

At column 5, line 41, "nmmol)" should read --mmol)--.

At column 6, line 22, "Methyl" should read --Preparation of Methyl--.

At column 7, line 13, "were evaporate" should read were evaporated--.

At column 10 lines 52-53, "trifluoro-methylfulfonyl" should read --trifluoromethylsulfonyl--.

At column 10, line 64 "with graded mixtures" should read with a graded mixture--.

At column 11, line 66, "-60-" should read -- -6-0- --.

At column 14, line 14, "dimethlformimide" should read --dimethylformamide--.

At column 15, line 30, "4-hydroxymethyl-α" should read --4-formyl-α --.

At column 15, lines 58-59, "4-trifluoro-methylsulfonyloxymethyl- α" should read --4-hydroxoymethyl- α --.

At column 16, line 33, "dissolve din" should read --dissolved in--.

At column 18, line 29, "Benxyl" should read --Benzyl--.

At column 18, line 64, "from" should read --form--.

At column 19, line 1, "glucopyranosyl β-D" should read --glucopyranosyl- α -D--

At column 23, line 60, "perchloride" should read --perchlorate--.

At column 24, line 8, "mehyl" should read --methyl--.

At column 24, line 25, "($H30$)" should read --($H^+$)--.

At column 24, line 34, "sulfonyloxmethyl" --sulfonyloxymethyl--.

UNITED STATES PATENT AND TRADEMARK OFFICE
CERTIFICATE OF CORRECTION

PATENT NO. : 5,097,023

DATED : March 17, 1992

INVENTOR(S) : Jean-Bernard Ducep and Charles Danzin

It is certified that error appears in the above-identified patent and that said Letters Patent is hereby corrected as shown below:

At column 24, line 58, "Methyl}4," should read --Methyl}1,4--.

At column 27, line 52, "1,4-[(2,3,4" should read --1,4-Dideoxy-1,4-[(2,3,4--.

At column 28, line 1, "6 β -D" should read --6- β -D--.

At column 29, line 10, "microscopy may" should read --microscopy, may--.

At column 30, line 17, claim 8, "glucopyranosyl]-1,4" should read --glucopyranosyl- α -D-glucopyranosyl]-1,4--.

At column 30, line 39, claim 14, "([4-deoxy" and --{[4-deoxy--.

At column 30, line 40, claim 14, "glucopyranosyl]methyl}-1,4" should read --glucopyranosyl)-4- α -D-glucopyranosyl]methyl}-1,4--.

Signed and Sealed this

Fourth Day of January, 1994

BRUCE LEHMAN

*Attest:*

*Attesting Officer*  *Commissioner of Patents and Trademarks*